(12) United States Patent
Dupont

(10) Patent No.: US 11,464,401 B2
(45) Date of Patent: Oct. 11, 2022

(54) OPTICALLY GUIDED SURGICAL DEVICES

(71) Applicant: Children's Medical Center Corporation, Boston, MA (US)

(72) Inventor: Pierre Dupont, Wellesley, MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

(21) Appl. No.: 16/776,775

(22) Filed: Jan. 30, 2020

(65) Prior Publication Data

US 2020/0245852 A1 Aug. 6, 2020

Related U.S. Application Data

(62) Division of application No. 15/158,475, filed on May 18, 2016, now abandoned.

(Continued)

(51) Int. Cl.
*A61B 1/018* (2006.01)
*A61B 1/00* (2006.01)
(Continued)

(52) U.S. Cl.
CPC .......... *A61B 1/018* (2013.01); *A61B 1/00087* (2013.01); *A61B 1/00089* (2013.01);
(Continued)

(58) Field of Classification Search
CPC . A61B 1/00089; A61B 1/00098; A61B 1/018; A61B 17/28; A61B 17/29; A61B 17/22031
See application file for complete search history.

(56) References Cited

U.S. PATENT DOCUMENTS

| 4,436,087 A | 3/1984 | Ouchi |
| 5,002,042 A * | 3/1991 | Okada ............... A61B 1/00089 |
| | | 600/127 |

(Continued)

FOREIGN PATENT DOCUMENTS

| EP | 1426072 | 10/2008 |
| EP | 2433551 | 3/2012 |

(Continued)

OTHER PUBLICATIONS

Ahmed et al., "Initial clinical experience with a novel visualization and virtual electrode radiofrequency ablation catheter to treat atrial flutter," Heart Rhythm Society, pp. 361-367, 2011.

(Continued)

*Primary Examiner* — Matthew J Kasztejna
(74) *Attorney, Agent, or Firm* — Fish & Richardson P.C.

(57) ABSTRACT

A device for performing surgical procedures, such as intra-cardiac procedures or neurosurgical procedures, includes a solid optical window formed of a transparent, compliant material, wherein the solid optical window includes a proximal side and a distal side, wherein a distal face of the solid optical window is configured to approach tissue during a surgical procedure; an imaging system embedded into the solid optical window and positioned to obtain an image through at least a portion of the distal face of the solid optical window; and a tool channel formed through the solid optical window from the proximal side to the distal side of the solid optical window, wherein the tool channel is configured to receive a tool for performing the surgical procedure.

14 Claims, 34 Drawing Sheets

Related U.S. Application Data

(60) Provisional application No. 62/182,204, filed on Jun. 19, 2015.

(51) Int. Cl.

| | | |
|---|---|---|
| *A61B 1/05* | (2006.01) | |
| *A61B 10/02* | (2006.01) | |
| *A61B 10/04* | (2006.01) | |
| *A61B 17/00* | (2006.01) | |
| *A61B 1/015* | (2006.01) | |

(52) U.S. Cl.
CPC ...... *A61B 1/00096* (2013.01); *A61B 1/00179* (2013.01); *A61B 1/015* (2013.01); *A61B 1/05* (2013.01); *A61B 10/02* (2013.01); *A61B 10/0283* (2013.01); *A61B 10/04* (2013.01); *A61B 17/00234* (2013.01); *A61B 2017/00243* (2013.01)

(56) References Cited

U.S. PATENT DOCUMENTS

| | | | |
|---|---|---|---|
| 5,025,778 | A | 6/1991 | Silverstein |
| 5,217,001 | A | 6/1993 | Nakao et al. |
| 5,261,391 | A | 11/1993 | Inoue |
| 5,300,087 | A * | 4/1994 | Knoepfler .............. A61B 17/29 604/33 |
| 5,454,807 | A | 10/1995 | Lennox et al. |
| 5,632,782 | A | 5/1997 | Adair |
| 5,660,175 | A | 8/1997 | Dayal |
| 5,855,569 | A | 1/1999 | Komi |
| 5,941,815 | A | 8/1999 | Chang |
| 6,315,714 | B1 | 11/2001 | Akiba |
| 6,419,626 | B1 * | 7/2002 | Yoon .................. A61B 1/00052 600/103 |
| 6,503,192 | B1 | 1/2003 | Ouchi |
| 6,749,559 | B1 | 6/2004 | Kraas et al. |
| 6,752,755 | B2 * | 6/2004 | Akiba .................. A61B 1/00096 600/127 |
| 7,442,167 | B2 | 10/2008 | Dunki-Jacobs et al. |
| 7,537,562 | B2 | 5/2009 | Takano |
| 7,914,444 | B2 | 3/2011 | Moriyama et al. |
| 8,133,239 | B2 * | 3/2012 | Oz ....................... A61B 17/122 606/142 |
| 8,287,447 | B2 | 10/2012 | Gasche et al. |
| 8,425,407 | B2 | 4/2013 | Sato et al. |
| 8,491,631 | B2 | 7/2013 | Del Nido et al. |
| 8,926,502 | B2 | 1/2015 | Levy et al. |
| 9,402,531 | B2 | 8/2016 | Chin |
| 9,451,875 | B2 | 9/2016 | Sigmon, Jr. |
| 9,459,442 | B2 | 10/2016 | Miller |
| 9,709,795 | B2 | 7/2017 | Miller |
| 2002/0068853 | A1 | 6/2002 | Adler |
| 2003/0093071 | A1 * | 5/2003 | Hauck ................. A61B 18/1442 606/41 |
| 2005/0197530 | A1 | 9/2005 | Wallace |
| 2006/0264708 | A1 | 11/2006 | Horne, Jr. |
| 2007/0066869 | A1 | 3/2007 | Hoffman |
| 2007/0299468 | A1 * | 12/2007 | Viola .................. A61B 5/0084 606/205 |
| 2009/0048486 | A1 | 2/2009 | Surti |
| 2009/0171373 | A1 * | 7/2009 | Farritor .................. A61B 90/37 606/130 |
| 2010/0286475 | A1 | 11/2010 | Robertson |
| 2011/0288372 | A1 | 11/2011 | Petersen |
| 2011/0295072 | A1 | 12/2011 | Boulais et al. |
| 2012/0209074 | A1 | 8/2012 | Titus |
| 2012/0232342 | A1 | 9/2012 | Reydel |
| 2013/0245371 | A1 | 9/2013 | Mourlas et al. |
| 2013/0281779 | A1 | 10/2013 | Robertson |
| 2014/0213847 | A1 | 7/2014 | Green et al. |
| 2014/0213848 | A1 | 7/2014 | Moskowitz et al. |
| 2014/0221749 | A1 | 8/2014 | Grant et al. |
| 2015/0065795 | A1 | 3/2015 | Titus |
| 2015/0313633 | A1 | 11/2015 | Gross et al. |
| 2016/0367120 | A1 | 12/2016 | Dupont et al. |
| 2018/0098850 | A1 * | 4/2018 | Rafiee ................ A61B 17/0487 |

FOREIGN PATENT DOCUMENTS

| | | |
|---|---|---|
| JP | 3793368 B2 | 7/2006 |
| WO | WO 2011/047339 | 4/2011 |

OTHER PUBLICATIONS

Ataollahi et al., "Cardioscopic Tool-Delivery Instrument for Beating-Heart Surgery," IEEE ASME Transactions on Mechatronics, 21(1):1-1 (abstract), Jan. 2015 [retrieved on Sep. 8, 2016]. Retrieved from the internet: <URL:https://www.researchgate.net/publication/283309805_Cardioscopic_Tool-Delivery_Instrument_for_Beating-Heart_Surgery>.

Extended European Search Report in European Application No. 16812547.4, dated Feb. 21, 2019, 106 pages.

Extended European Search Report in European Application No. 17750861.1, dated Sep. 30, 2019, 7 pages.

International Preliminary Report on Patentability in International Application No. PCT/US2016/038147, dated Dec. 19, 2017, 9 pages.

International Preliminary Report on Patentability in International Application No. PCT/US2017/017446, dated Aug. 14, 2018, 8 pages.

International Search Report and Written Opinion in International Application No. PCT/US17/17445, dated May 5, 2017, 10 pages.

International Search Report and Written Opinion in International Application No. PCT/US2016/038147, dated Sep. 8, 2016, 11 pages.

P. Dupont; "Invention Disclosure—Cardioscopes"; May 21, 2016; 5 pages.

Padala et al., "Transapical beating heart cardioscopy technique for off-pump visualization of heart valves," The Journal of thoracic and Cardiovascular Surgery, 144(1):231-234, 2012.

Shiose et al., "Cardioscopy-guided surgery: Intracardiac mitral and tricuspid valve repair under direct visualization in the beating heart," The Journal of thoracic and Cardiovascular Surgery, 142(1):199-202, 2011.

Uchida, "Recent Advances in Percutaneous Cardioscopy," Curr Cardiovasc Imaging Rep, pp. 317-327, May 12, 2011.

Vasilyev et al., "A novel cardioport for beating-heart, image-guided intracardiac surgery" The Journal of thoracic and Cardiovascular Surgery, 142(6):1545-1551, Dec. 2011.

Vasilyev et al., "Three-Dimensional Echo and Videocardioscopy-Guided Atrial Septal Defect Closure," Annals of Thoracic Surgery, 82:1322-1326, 2006.

Vasilyev et al.; "A Novel Cardioport for Beating-Heart Image-Guided Intracardiac Surgery"; Children's Hospital Boston, Harvard Medical School, Boston, Massachusetts Institute of Technology, Cambridge, Massachusetts; International Society tor Minimally Invasive Cardiothoracic Surgery (ISMICS); Jun. 3, 2009; 17 pages.

\* cited by examiner

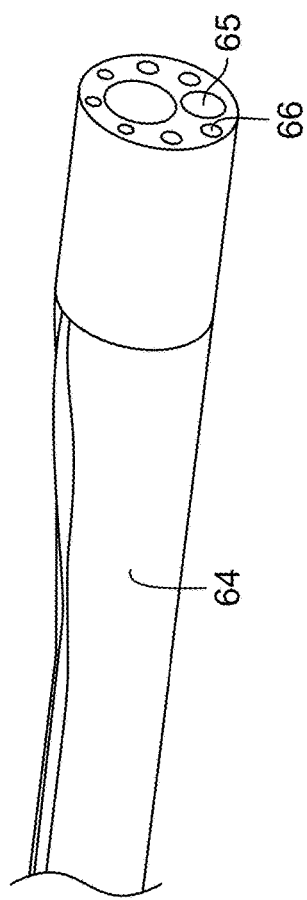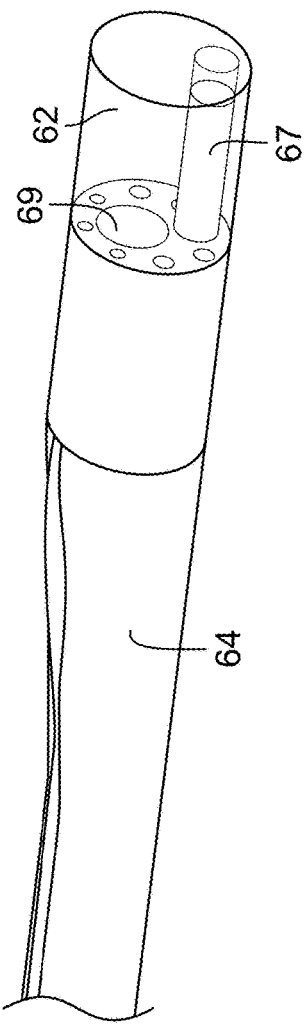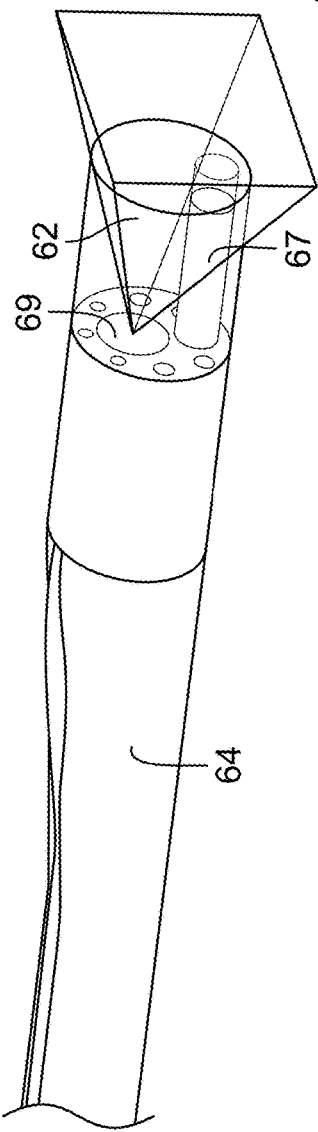

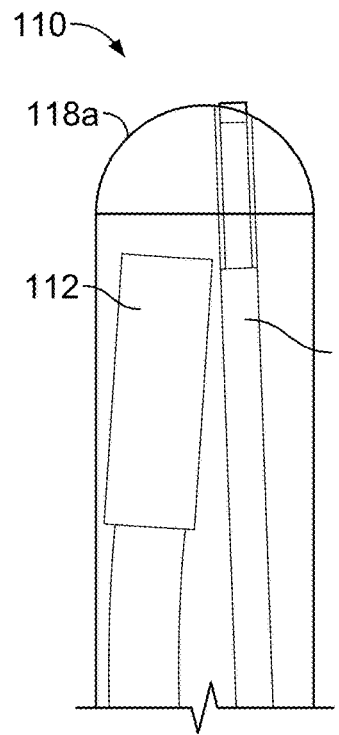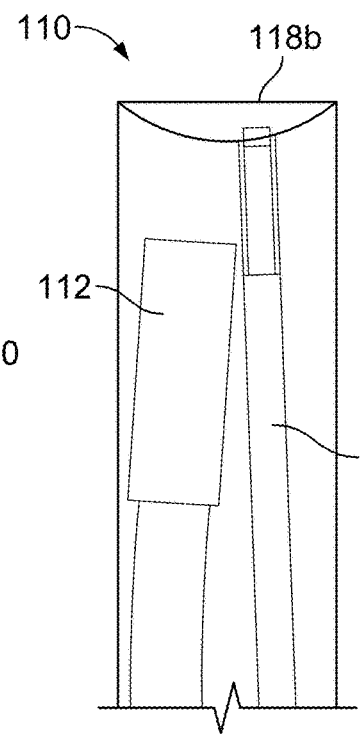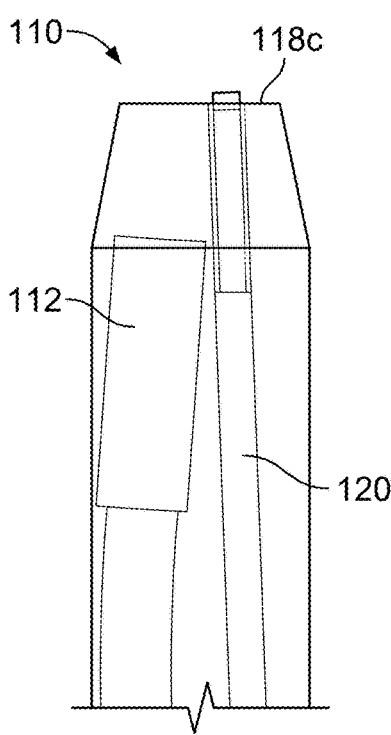
FIG. 8A          FIG. 8B          FIG. 8C
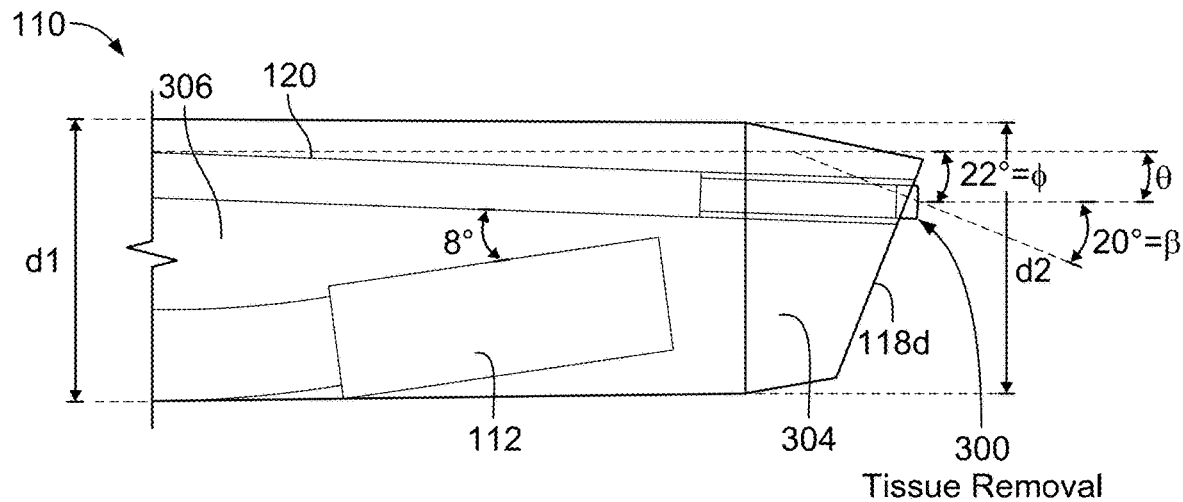
FIG. 8D

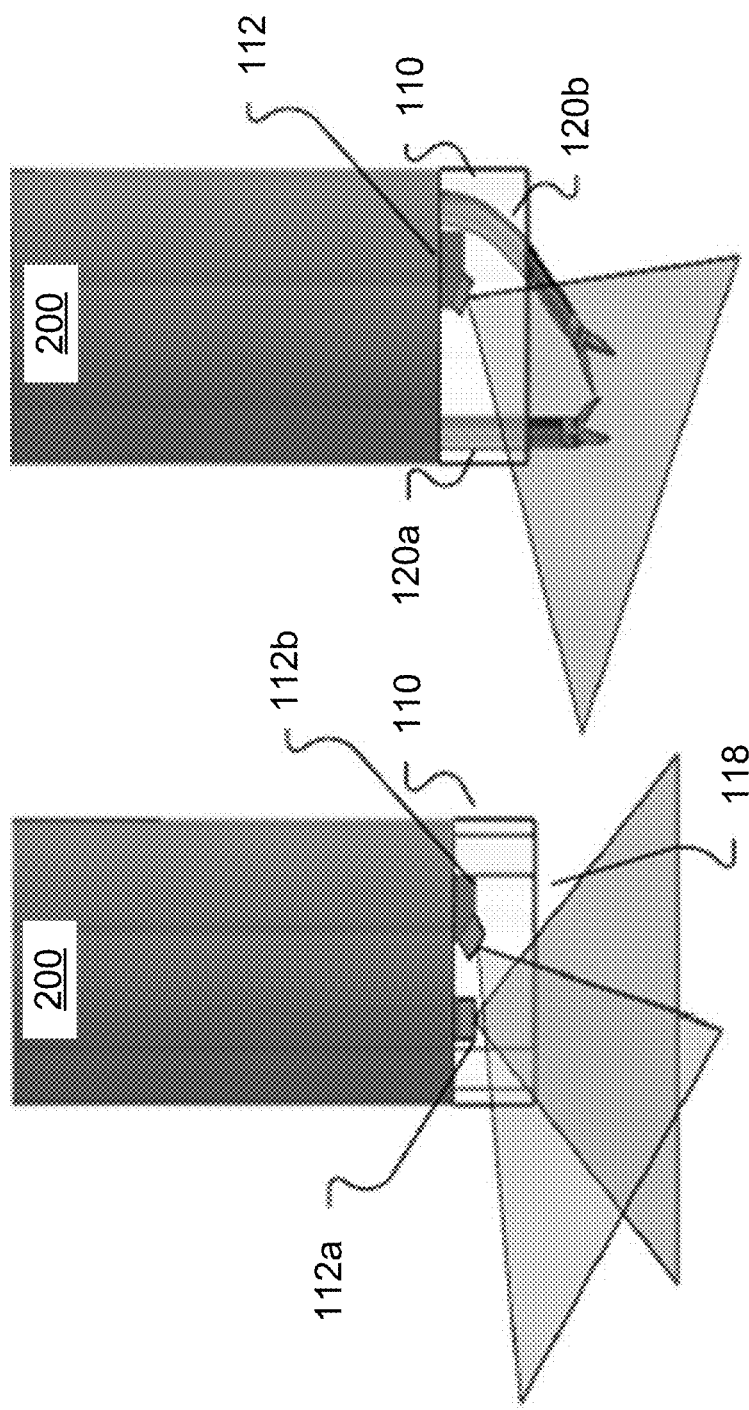

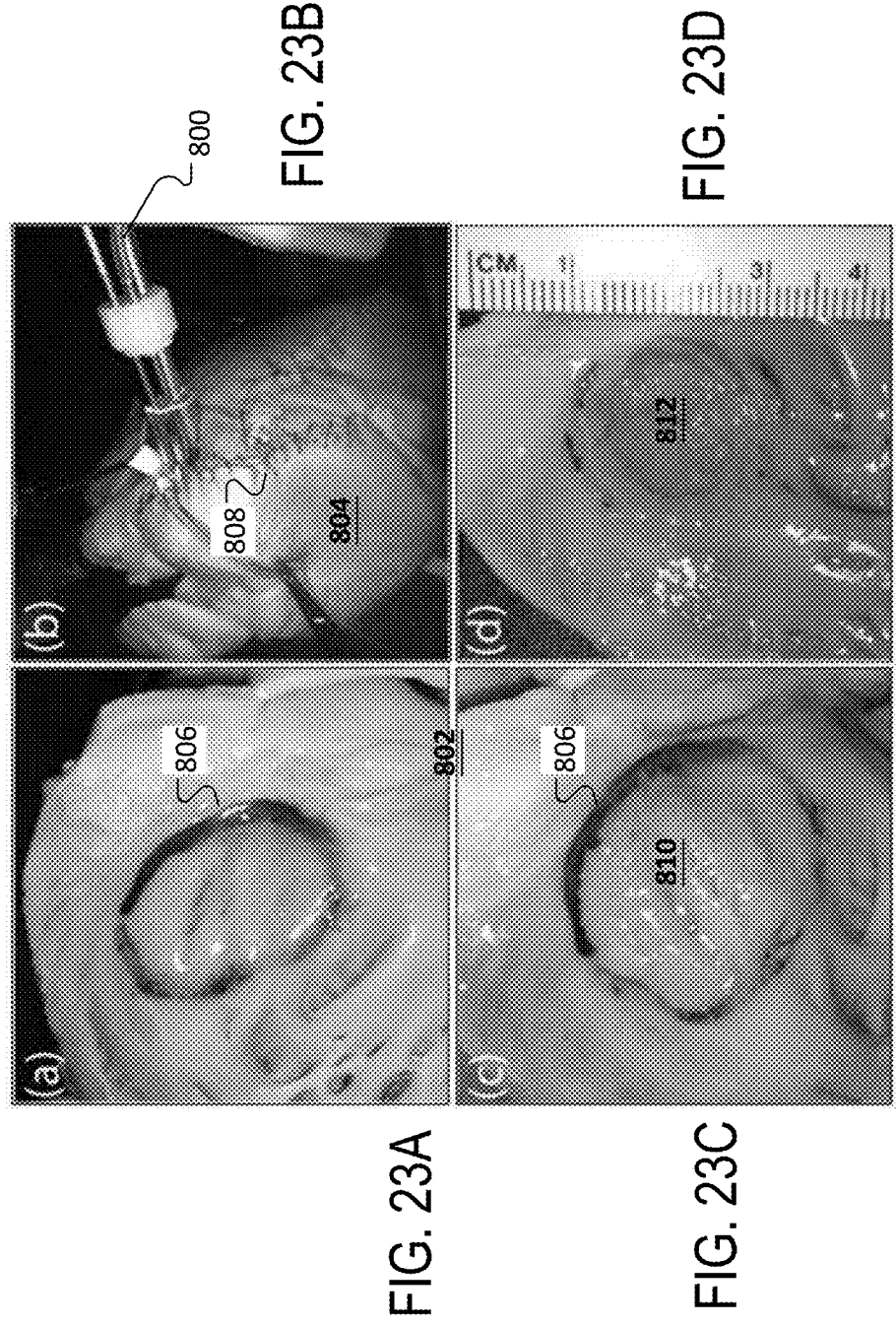

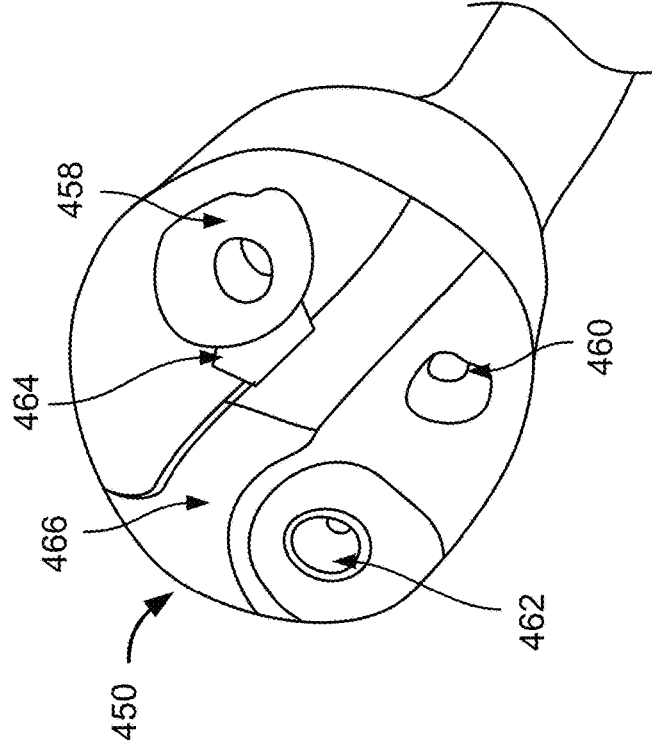
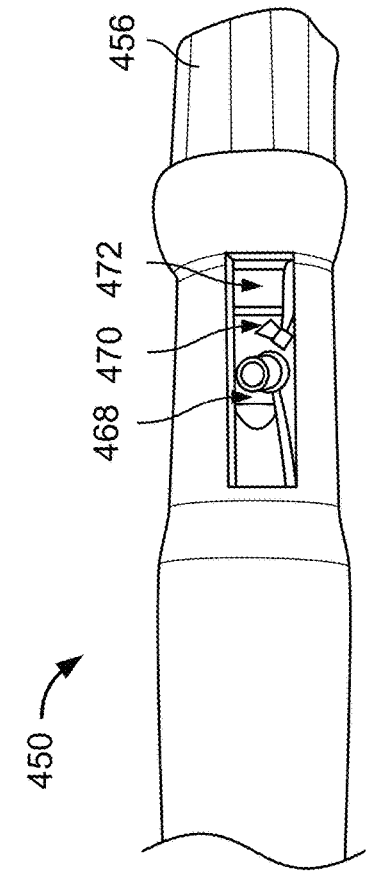
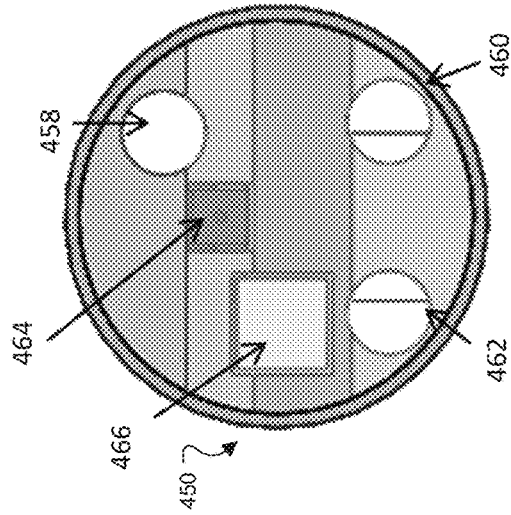
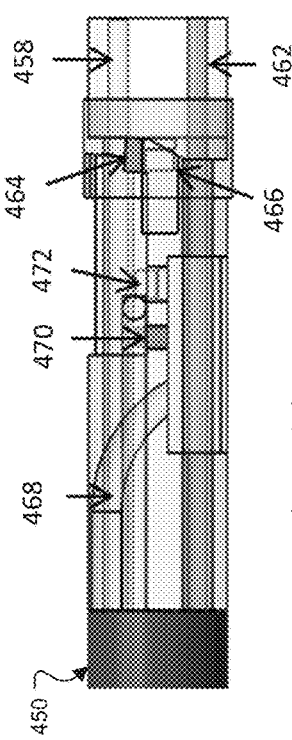
FIG. 28B
FIG. 28D
FIG. 28A
FIG. 28C

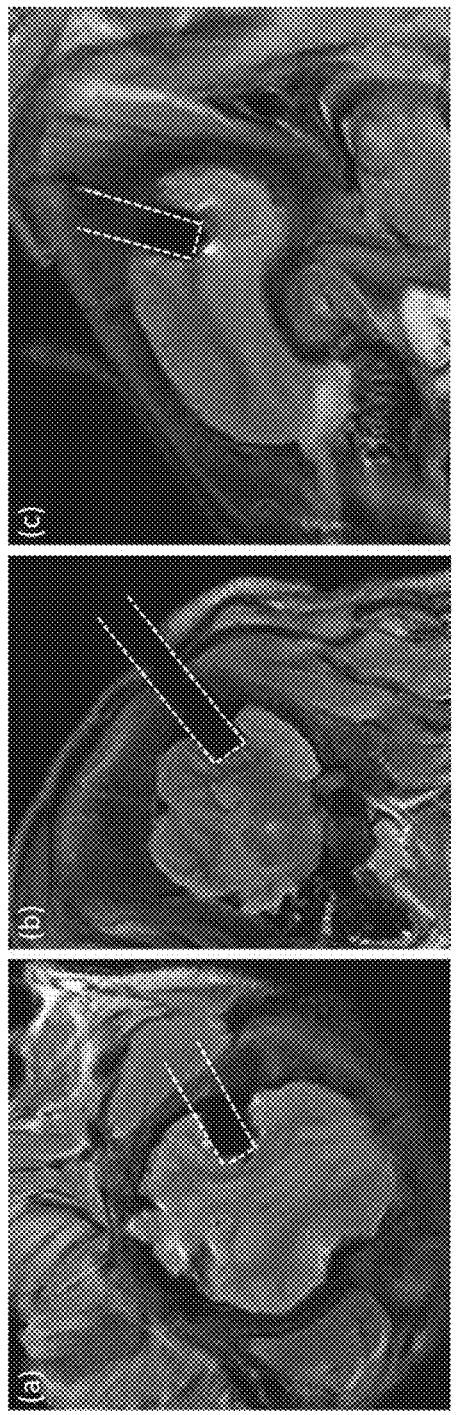
FIG. 30
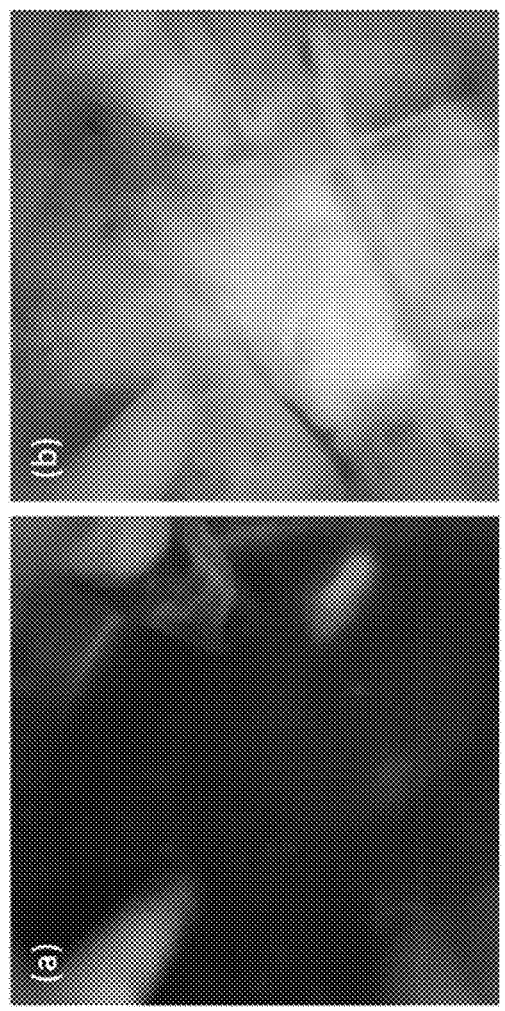
FIG. 31B
FIG. 31A

OPTICALLY GUIDED SURGICAL DEVICES

CLAIM OF PRIORITY

This application is a divisional of U.S. patent application Ser. No. 15/158,475, filed on May 18, 2016, which claims priority to U.S. Provisional Application Ser. No. 62/182,204, filed on Jun. 19, 2015, the contents of which are incorporated here by reference in their entirety.

STATEMENT AS TO FEDERALLY SPONSORED RESEARCH

This invention was made with Government support under Grant No. R01HL124020 awarded by the National Institutes of Health. The Government has certain rights in the invention.

FIELD OF THE INVENTION

The invention relates to devices and methods for surgical imaging, such as during an intracardiac or neurosurgical procedure.

BACKGROUND

Vascular heart disease is an important health problem afflicting over 2.5% of the U.S. population. A variety of percutaneous and transcardiac procedures for valve replacement have been developed. Catheter-based interventions provide a relatively low-risk opportunity to intervene earlier in the disease process, as well as in the sickest patients, while avoiding the risks of cardiopulmonary bypass. Procedures that can be performed via catheter include transcatheter aortic valve replacement and catheter-delivered clips to reduce or eliminate mitral valve regurgitation. Beating-heart interventions also provide the opportunity for continuous intra-operative assessment of the repair. Catheter-based or endoscopic interventions can also be used for other medical procedures, such as neurosurgical procedures.

SUMMARY

This disclosure is based, at least in part, on the discovery that surgical procedures, such as intracardiac procedures or neurosurgical procedures, can be guided by imaging provided through an optical window integrated on the distal tip of an instrument to be inserted into a surgical site, such as into a beating heart or into brain tissue. Imaging at the surgical site (e.g., within the heart or brain) before, during, and after a procedure provides for image-guided positioning of instruments or of tools or devices guided by or inserted by the instrument, such as a tissue removal tool, a catheter, a tissue gripping device, a mitral valve clip, or another tool. Imaging at the surgical site can also enable reliable detection of contact between the instrument, tool, or device and the target tissue, as well as the ability to stabilize and control the position of the instrument, tool, or device relative to the target tissue. Once the instrument, tool or device is positioned, procedures, such as procedures within the beating heart or neurosurgical procedures, can be carried out under image guidance, and the result of the procedure can be visualized in vivo and in real time.

In an aspect, a device for performing surgical procedures includes a solid optical window formed of a transparent, compliant material, wherein the solid optical window includes a proximal side and a distal side, wherein a distal face of the solid optical window is configured to approach tissue during a surgical procedure; an imaging system embedded into the solid optical window and positioned to obtain an image through at least a portion of the distal face of the solid optical window; and a tool channel formed through the solid optical window from the proximal side to the distal side of the solid optical window, wherein the tool channel is configured to receive a tool for performing the surgical procedure.

Embodiments can include one or more of the following features.

The solid optical window is formed from a polymer.

The solid optical window is formed from silicone or silicone rubber.

The distal face of the solid optical window is planar.

A normal to the distal face of the solid optical window is disposed at an angle greater than 0° relative to a longitudinal axis of the solid optical window.

The normal to the distal face is disposed at an angle of between 20-25° relative to the longitudinal axis of the solid optical window.

A first diameter of a proximal portion of the solid optical window is greater than a second diameter of a distal portion of the solid optical window.

The imaging system is embedded in the proximal portion of the solid optical window.

The imaging system includes a camera or an optical fiber, such as one or more cameras or optical fibers.

The imaging system includes one or more illumination devices.

When no tool is present in the tool channel, the tool channel is sealed.

When no tool is present in the tool channel, the tool channel appears as a thin line in an image acquired by the imaging system.

When no tool is present in the tool channel, the tool channel collapses closed.

The tool channel is offset laterally relative to a central axis of the solid optical window.

A longitudinal axis of the tool channel is disposed at an angle between 0° and 90° relative to a longitudinal axis of the solid optical window.

A longitudinal axis of the tool channel is disposed at an angle greater than 0° relative to a longitudinal axis of a distal portion of the imaging system.

The device includes a tube disposed in a proximal portion of the tool channel.

The tube is formed of a rigid material.

The tube is disposed outside of a field of view of the imaging system.

The surgical procedure includes an intracardiac procedure. The distal face of the solid optical window is configured to come into contact with cardiac tissue.

The tool for performing an intracardiac procedure includes a tissue removal tool.

The device is mounted on or integrated into a distal end of a catheter.

The tool for performing an intracardiac procedure includes a tissue gripping device.

The tool for performing an intracardiac procedure includes one or more clips configured to be attached to a cardiac valve leaflet.

The surgical procedure includes a neurosurgical procedure. The distal face of the solid optical window is configured to come into contact with brain tissue.

The device is mounted on or integrated into a distal end of a neuroendoscope.

The device is mounted on or integrated into a lateral surface of a neuroendoscope.

The device includes a flushing channel formed through the solid optical window from the proximal face to the distal face of the solid optical window.

The flushing channel is configured to eject a liquid from an opening in the distal face of the solid optical window.

The device includes a tube disposed in a proximal portion of the flushing channel.

The tube is disposed outside of a field of view of the imaging system.

When no liquid is present in the flushing channel, the flushing channel is sealed.

When no liquid is present in the flushing channel, the flushing channel appears as a thin line in an image acquired by the imaging system.

The device includes multiple tool channels formed through the solid optical window.

A longitudinal axis of a first one of the multiple tool channels is disposed at an angle greater than 0° relative to a longitudinal axis of a second one of the multiple tool channels.

The imaging system is positioned to obtain an image of a distal opening of one or more of the multiple tool channels.

The multiple tool channels are positioned such that the tools received by the multiple tool channels meet at a surgical site, and wherein the imaging system is positioned to obtain an image of the tools meeting at the surgical site.

In a general aspect, a method for performing a surgical procedure includes inserting an instrument into a patient, the instrument including a solid optical window at a distal end of the instrument, the solid optical window formed of a transparent, compliant material; causing a distal face of the solid optical window to come approach tissue of the patient; inserting a tool through a tool channel in the solid optical window, the tool channel formed through the solid optical window from a proximal side to a distal side of the solid optical window; and obtaining an image of the tissue, the tool, or both through at least a portion of the distal face of the solid optical window.

Embodiments can include one or more of the following features.

The instrument includes a catheter.

The method includes performing a beating heart intracardiac procedure using the tool.

The beating heart intracardiac procedure includes a valve repair.

Causing the distal face of the solid optical window to approach tissue of the patient comprises causing the distal face of the solid optical window to come into contact with the tissue.

The method includes performing a neurosurgical procedure using the tool.

Obtaining an image includes obtaining an image of the tissue prior to causing the distal face of the solid optical window to come into contact with the tissue.

The method includes controlling a depth of penetration of the tool into the tissue.

The method includes controlling an angle between the tool and the tissue.

A device for performing surgical procedures includes a hollow optical window formed of a transparent, compliant material. The hollow optical window is configured to be filled with saline. A distal face of the solid optical window is configured to approach tissue during a surgical procedure. The hollow optical window is disposed on a distal end of an instrument. The device includes an imaging system in the instrument and positioned to obtain an image through at least a portion of the distal face of the hollow optical window. The device includes a tool channel formed through the instrument and configured to receive a tool for performing the surgical procedure. The hollow optical window is configured to allow the tool to pass through the window to perform the surgical procedure.

Embodiments can include one or more of the following features.

A position at which the tool passes through the window can be adjusted.

A position of the imaging system in the instrument can be adjusted.

The hollow optical window is configured to expand when filled with saline.

The devices and methods for cardiac imaging described herein can have one or more of the following advantages. The device can be manipulated, stabilized, and positioned relative to the target tissue, such as cardiac tissue in a beating heart, for precise control of tool operation. For instance, in some examples, tissue contact with the optical window allows the depth of penetration of a tool into tissue or the contact angle of the tool with tissue of a beating heart to be precisely controlled, thus reducing the likelihood of both damage to the tissue, such as accidental damage of sensitive heart structures or perforation of the heart wall, and damage to the tool.

A large field of view is available that is only minimally occluded when no tool has been inserted into the optical window, thus enabling clear visualization at and in the vicinity of the target tissue. The optical window provides the ability to obtain high resolution (e.g., sub-millimeter resolution), in vivo images of device deployment and function in a beating heart and of detailed anatomy of the target tissue before, during, and after a procedure. A clear view can be achieved without continuous saline infusion during imaging, and there is a low likelihood of leakage into or out of the optical window. Light reflection from surfaces and interfaces is low and thus high image quality, low image deformation, and good focus can be obtained. The optical window is inexpensive to fabricate and can be sized for integration into a variety of devices for in vivo intracardiac procedures.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 7A-7C are diagrams of an example instrument having an optical window.

FIGS. 8A-8D are diagrams of various examples of the optical window.

FIG. 9A is a diagram of an optical window having two cameras.

FIG. 9B is a diagram of an optical window having two tool channels.

FIGS. 23A-23D are photographs of tissue removal in an ex vivo beating heart experiment.

FIGS. 28A-28D are diagrams of a multi-port neuroendoscope having a distal optical window and a lateral optical window.

FIG. 30 shows images of a multi-port neuroendoscope inside a porcine brain.

FIGS. 31A and 31B are photographs of tissue visualization by a multi-port neuroendoscope.

DETAILED DESCRIPTION

Figure 1:
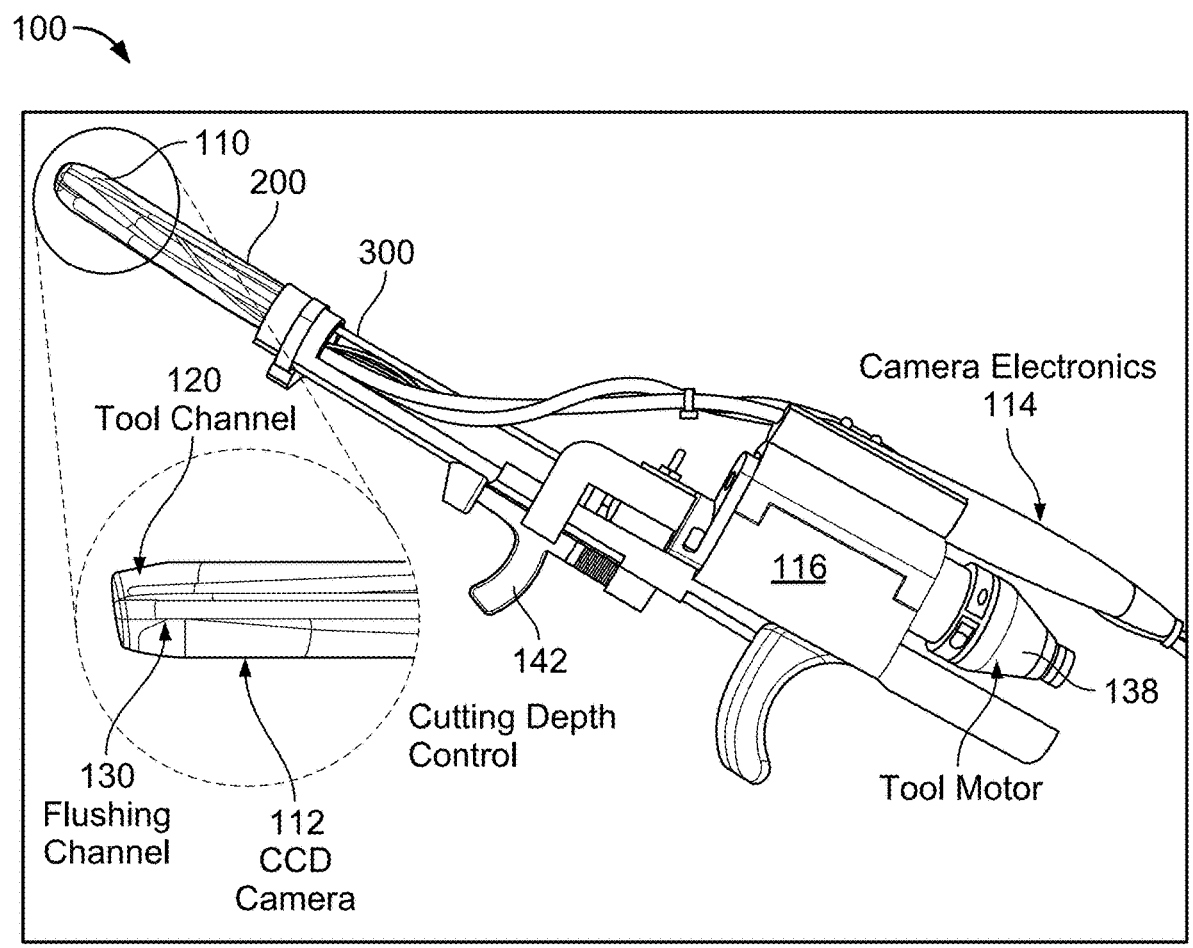
FIG. 1 is a diagram of an instrument for image-guided intracardiac procedures.

Referring to FIG. 1, a handheld instrument 100 for image-guided intracardiac procedures includes a distal imaging system 200 and a tool 300, such as a tissue removal tool, a catheter, a tissue gripping device, a mitral valve clip, or another type of tool. The imaging system 200, sometimes referred to as a cardioscope, includes an optically clear window 110 within which a camera 112 or optical fiber and an illumination device (not shown) are disposed. The camera 112 and illumination device are controlled by electronics 114, which can be in a handle 116 of the instrument 100 or external to the instrument. The camera 112 and illumination device in the cardioscope 200 enable the procedure site to be imaged, for instance, to assist with detection of contact between a distal face 118 of the optically clear window 110 (sometimes referred to as an optical window) and the tissue, navigation to a desired site, or visualization of the site during or after the procedure.

The tool 300 passes through a tool channel 120 in the optical window 110 and exits through the distal face 118 of the optical window 110. The handle 116 enables a user, such as a surgeon, to precisely control the location and operation of the tool 300. The optical window 110 also includes a flushing channel 130 through which fluid, such as saline, can be provided. The fluid can be used to flush the interface between the distal face 118 of the optical window 110 and the tissue, or can be used for diagnostic purposes, as discussed below.

Device Components

Blood is opaque to visible light. To image in a blood-filled environment, such as a beating heart or a brain, using visible light, blood can be excluded from the space between the imaging device and the tissue being imaged. An optical window is a device that creates an optically transparent pathway between an imaging device, such as a camera or an optical fiber, and tissue. The optical window described here is a device formed of a solid, transparent polymer having a distal face that can conform to the topology of the tissue, thus displacing blood from the interface between the distal face and the tissue. As a result, an optically clear path for imaging the tissue is created.

Figure 2:
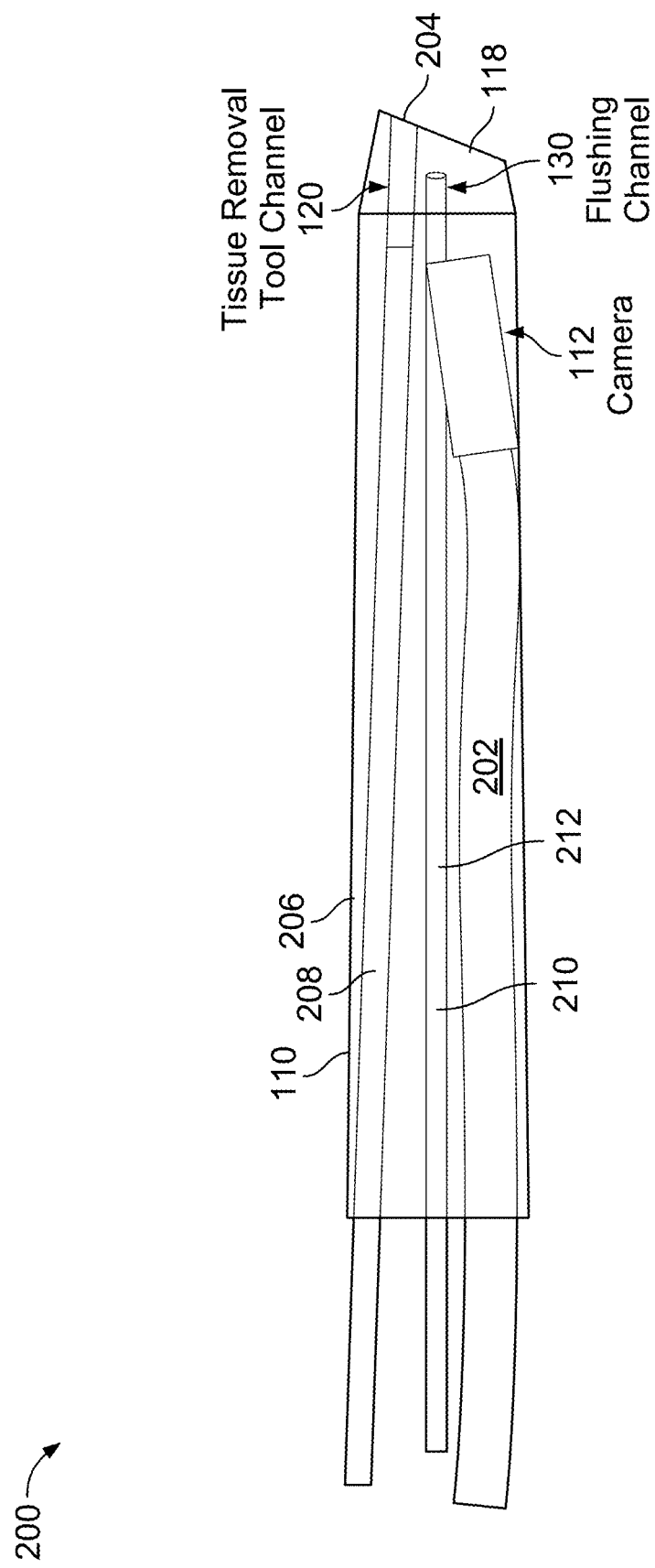
FIG. 2 is a diagram of an optical window for an instrument for image-guided intracardiac procedures.

Referring to FIG. 2, the optical window 110 of the cardioscope 200 is a solid window formed of a transparent, compliant, biocompatible material, such as a polymer (e.g., silicone, silicone rubber, castable resins such as acrylic resins or polyurethanes, or another polymer), glass, transparent crystals, or another transparent, compliant material. The compliance of the optical window 110 can be controlled by the thickness and composition of the polymer and the conditions under which the polymer is processed, such as the curing temperature. The compliance of the optical window 110 helps facilitate contact with and imaging of irregular surfaces, as discussed below, and further helps to prevent damage to tissue. In the example of FIG. 2, the optical window 110 acts as a structural support for the components therein. In some examples, an optical window includes separate structural components. The optical window 110 can be formed of a material having a refractive index that is similar to the refractive index of the flushing fluid or to the environment in which the cardioscope 200 is to be deployed. In a specific example, the optical window 110 is formed of optically clear silicone (QSil 216 or QSil218 RTV-2 silicone rubber, Quantum Silicones LLC, Richmond, Va.) with a refractive index of about 1.4. The example of FIG. 2 shows the optical window 110 disposed at the distal end of a cardioscope. The optical window 110 can also be disposed on other surgical devices, such as neuroendoscopes, as discussed further below.

In the example of FIG. 2 the camera 112 and an illumination device, such as a light-emitting diode (LED) or optical fiber, are embedded within the solid material of the optical window 110. The camera 112 can be, for instance, a charge-coupled device (CCD) camera (e.g., a 5 mm diameter CCD camera) or a complementary metal-oxide semiconductor (CMOS) camera (e.g., a 1 mm×1 mm×1 mm CMOS video camera (250×250 pixels, Naneye, Awaiba, Inc., Funchal, Madeira, Portugal)). The illumination device can be a light-emitting diode (LED) or an optical fiber, such as a 1.6 mm×1.6 mm LED (Cree Inc., Durham, N.C.). The camera 112 and the illumination device can be connected to control electronics or storage devices by way of a cable 202. The camera 112 is positioned within the optical window 110 such that some or all of the distal face 118 of the optical window 110 falls within the field of view of the camera 112. The camera can have a large focal depth in order to enable high resolution imaging. In some examples, the camera 112 and illumination device are inserted into an optical channel formed in the optical window. In some examples, the camera 112 is a camera on a chip, e.g., a 1 mm² chip, with LED illumination. In some examples, the lens systems of the camera 112 and illumination device are designed to be focus-free such that a sharp image can be obtained over a large depth of field.

The use of a CMOS camera can have advantages. For instance, in a CMOS sensor, each pixel has its own charge-to-voltage conversion, and the sensor often also includes amplifiers, noise-correction, and digitization circuits, so that the chip outputs digital bits. This lowers camera cost while providing faster readout, lower power consumption, higher noise immunity and a smaller system size.

The distal face 118 of the optical window 110 displaces blood when pressed against tissue in a body cavity filled with an opaque fluid, such as the beating heart or a blood-filled cavity in the brain, thus enabling visualization of the interaction between the tool inserted in the tool channel 120 and the tissue (e.g., cardiac tissue or brain tissue). The compliance of the optical window 110 allows the distal face 118 of the optical window 110 to conform to irregular surfaces, thus effectively displacing blood from between the distal face 118 of the optical window 110 and the tissue. For instance, when the instrument 100 is used for repair of a paravulvular leak, the distal face 118 of the optical window 100 may come into contact with irregular tissue topography at the junction between the valve and surrounding cardiac tissue. The compliance of the optical window allows the distal face 118 of the optical window 110 to conform to that irregular topography, thus facilitating imaging and enabling precise control of the tool 300.

Figure 3A:
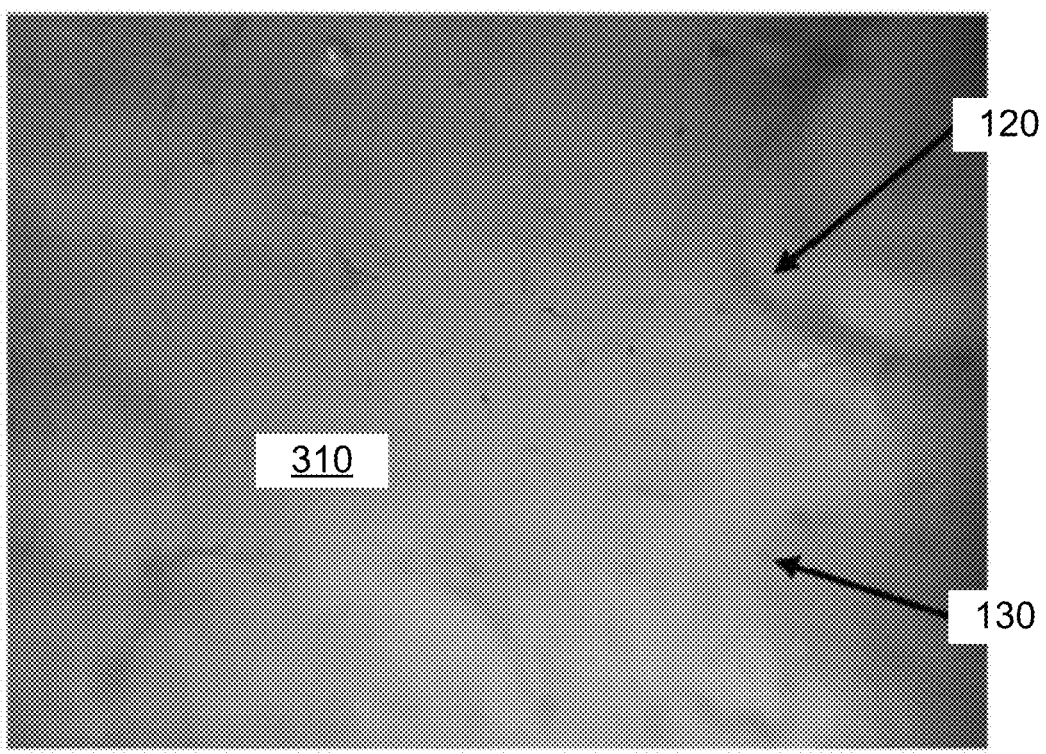
FIGS. 3A and 3B are photographs taken during use of an optical window.
Figure 3B:
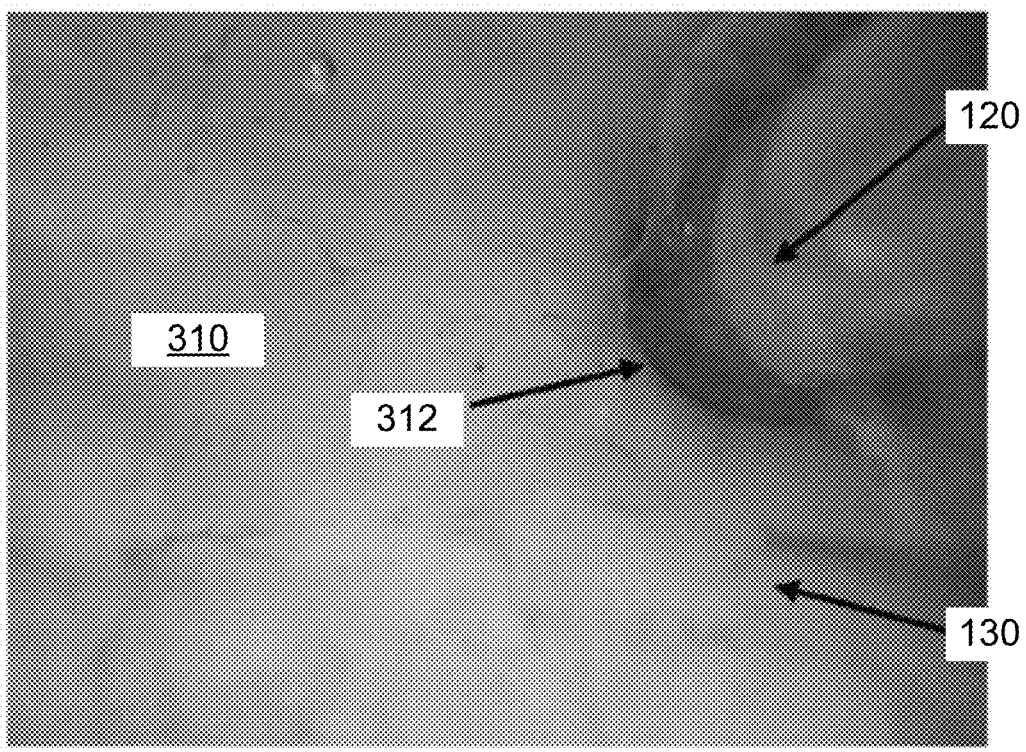

The tool channel 120 and the flushing channel 130 are elongated holes formed in the solid optical window 110. In some examples, due to the compliance of the material of the optical window 110, when empty, the tool channel 120 and the flushing channel 130 collapse onto themselves, forming a thin crack in the solid material of the optical window 110. The thin crack only minimally occludes the field of view of the camera 112, enabling the camera to image all of the tissue in the field of view prior to tool insertion into the tool channel 120. Referring to FIGS. 3A and 3B, in an example, a chicken breast 310 is manipulated by an instrument having an optical window at its distal end. Prior to tool insertion into the tool channel 120 (FIG. 3A), the tool channel 120 and the flushing channel 130 are almost invisible in the image acquired by the camera in the optical window, apparent as only thin lines. When a tool 312 is inserted into the tool channel 120, the tool appears in the image (FIG. 3B), thus occluding a portion of the field of view. In some examples, the tool channel 120 is filled with saline prior to tool insertion into the tool channel 120.

In some examples, the distal opening of the flushing channel 130 is self-sealing, preventing exchange of material, such as air or blood, between the interior of the flushing channel 130 and the heart. In some examples, the distal opening of the tool channel 120 seals upon insertion of a tool into the tool channel 120. In some examples, a seal, such as a silicone seal, is positioned at the distal opening of the tool channel 120, the flushing channel 130, or both, to seal the channels 120, 130 against material exchange.

Liquid, such as saline, can be provided through the flushing channel 130. Since the refractive index of silicone is close to the refractive index of water, filling the flushing channel 130 of a silicone optical window 110 causes the flushing channel 130 and the optical window 110 to have substantially the same refractive index, thus rendering the flushing channel almost transparent in images acquired by the camera 112.

In some examples, saline can be used to clear away blood trapped between the distal face 118 of the optical window 110 and the cardiac tissue. Blood can sometimes become trapped between the distal face 118 of the optical window 110 and the cardiac tissue when operating on uneven surfaces, such as trabeculated tissue, or when searching for a paravulvular leak at the junction between a valve annulus and the frame of an implanted valve. Liquid can also be provided through the flushing channel 130 to temporarily displace blood in front of the distal face 118 of the optical window 110 when the distal face 118 is not in contact with tissue. A bolus of saline can be ejected, allowing temporary visualization of structures located a short distance, such as a few mm, in front of the distal face 118 and helping to facilitate safe, precise navigation and avoidance of sensitive structures.

The optical window 110 can be fully sealed and internal components fully encapsulated such that blood from the heart does not leak into the channels 120, 130 or the camera 112 or other optical components and so that the environment of the heart is not exposed to air bubbles or non-sterile components in the optical window 110.

A distal portion 204 of the tool channel 120 can have a diameter that is closely matched with the outer diameter of the tool to achieve a tight seal around the tool, e.g., to minimize leakage of blood and air into and out of the tool channel 120. For instance, distal portion 204 of the tool channel 120 can have a diameter of about 1 mm, about 1.5 mm, about 2 mm, about 2.5 mm, or another diameter that is matched with the diameter of the tool 300.

The compliance of the optical window 110 allows the optical window 110 to deform to follow the shape of a tool inserted into the tool channel 120 or to follow the shape of the optical components.

In some examples, the tool channel 120 can be structured to act as a steering mechanism that is able to be deformed to point in a desired direction. For instance, the tool channel 120 can be formed of two pre-curved concentric elastic tubes. Twisting the internal tube can cause the optical window 110 to change shape to the configuration prescribed by the twisting tubes. The longitudinal extension of the tubes provides structural stability to the optical window 110 along its longitudinal axis.

In some examples, a proximal portion 206 of the tool channel 120 can be lined with a tube 208, such as a rigid tube formed of a biocompatible material, e.g., stainless steel, hard plastic, or other polymeric materials such as polytetrafluoroethylene (PTFE) that can reduce friction between the surface of the tool channel 120 and the tool inserted therein, thus enabling precise control of tool operation using small forces. For instance, the cutting depth of a tissue removal tool can be precisely adjusted by application of small forces. The inner diameter of the tube 208 can be the same as or slightly larger than the diameter of the distal portion 204 of the tool channel 120. For instance, the tube 208 can have an inner diameter of about 1.5 mm, about 2 mm, about 2.5 mm, about 3 mm, or another diameter. In some examples, the tube 208 can be formed of a compliant material.

In a specific example, the tool is a tissue removal tool as described below having an outer diameter of 2 mm, the distal portion 312 of the tool channel 120 has a diameter of 1.9 mm, and the tube 208 has an inner diameter of 2.15 mm.

The tube 208 can be positioned along the tool channel 120 proximal to the distal face 118 of the optical window 110 such that the tube 208 does not occlude the field of view of the camera 112. For instance, the distal end of the tube 208 can be located about 5 mm, about 6 mm, about 7 mm, about 8 mm, about 9 mm, about 10 mm, about 11 mm, about 12 mm, about 13 mm, about 14 mm, about 15 mm, or another distance from the distal face 118 of the optical window 110.

In some examples, a proximal portion 210 of the flushing channel 130 can be lined with a tube 212, such as a rigid tube formed of a biocompatible material, e.g., stainless steel. The tube 212 can be positioned along the flushing channel 130 proximal to the distal face 118 of the optical window 110 such that the tube 212 does not occlude the field of view of the camera 112. The distal end of the tube 212 in the flushing channel 130 can be positioned closer to the distal face 118 of the optical window 110 than the distal end of the tube 208 in the tool channel 120. For instance, the distal end of the tube 212 can be located about 3 mm, about 4 mm, about 5 mm, about 6 mm, about 7 mm, about 8 mm, about 9 mm, about 10 mm, or another distance from the distal face 118 of the optical window. In some examples, the tube can be formed of a compliant material.

Figure 4:
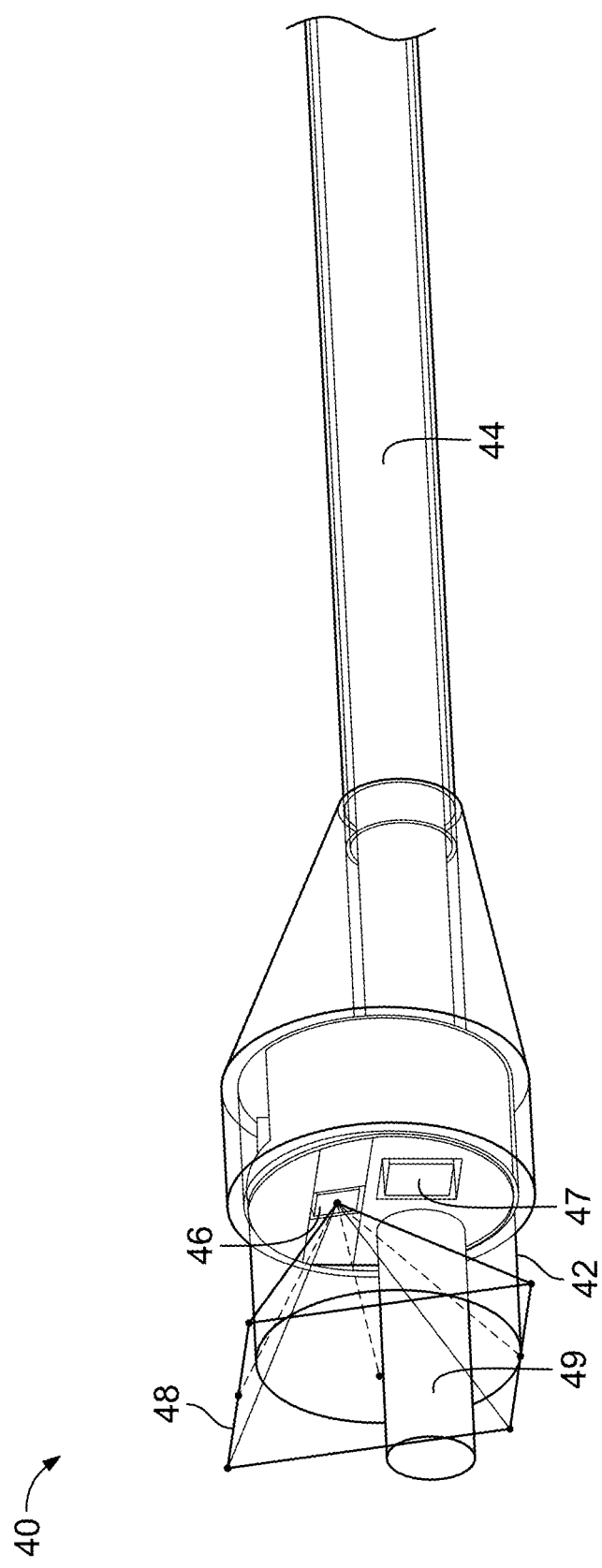
FIGS. 4-6 are diagrams of example instruments having optical windows.
Figure 5:
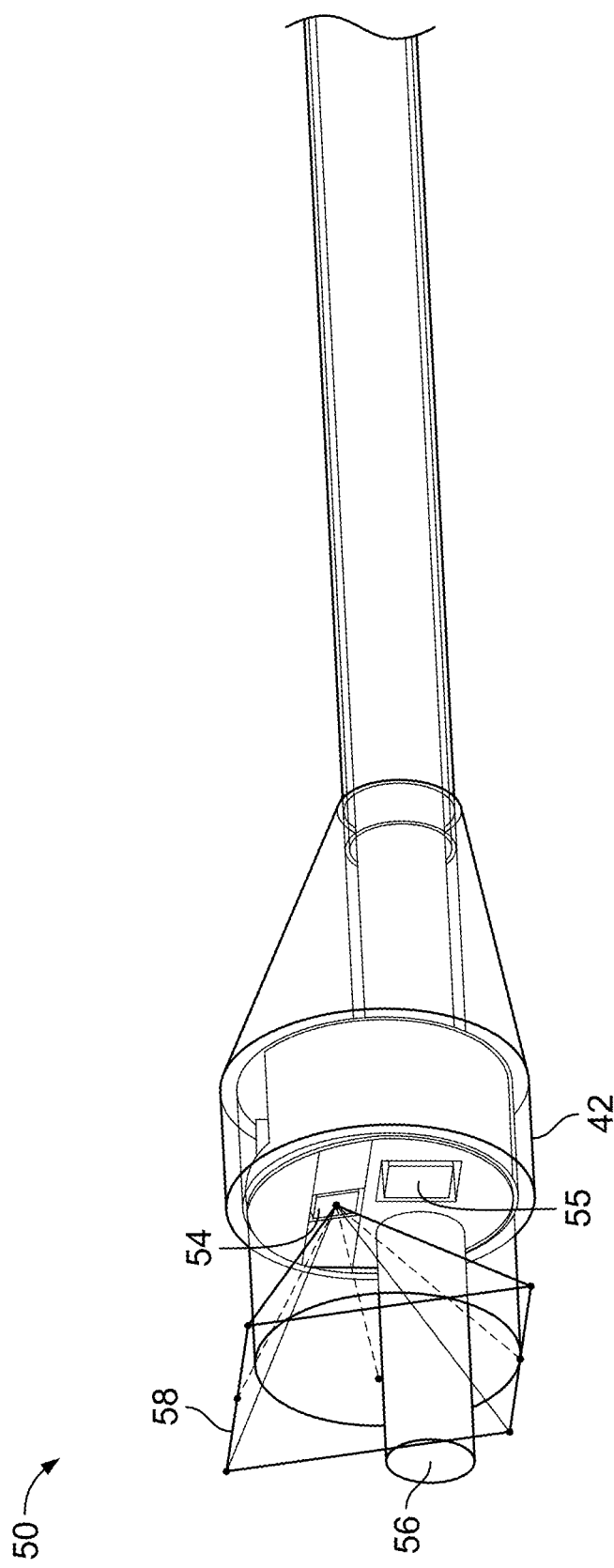

FIGS. 4-7 show alternative examples of cardioscopes and optical windows. Referring to FIG. 4, in a cardioscope 40, an optical window 42 is mounted on a 3 mm diameter straight tube 44. The cardioscope 40 includes a camera 46 on a chip having a field of view 48 as shown and an LED light source 47. A tool channel 49 falls within the field of view 48 of the camera 46. The cardioscope 40 can be, for instance, mounted on the distal end of a catheter, as discussed below. Referring to FIG. 5, a cardioscope 50 for mounting on the distal end of a catheter includes structural components 52 that constrain the position and angle of a camera 54 on a chip, an LED light source 55, and a tool channel 56. The outer diameter of the structural components 52 can be, e.g., 7 mm and the outer diameter of the tool channel 56 can be 3 mm. A field of view 58 of the camera 54 is not obstructed by the tool channel 56.

Figure 6:
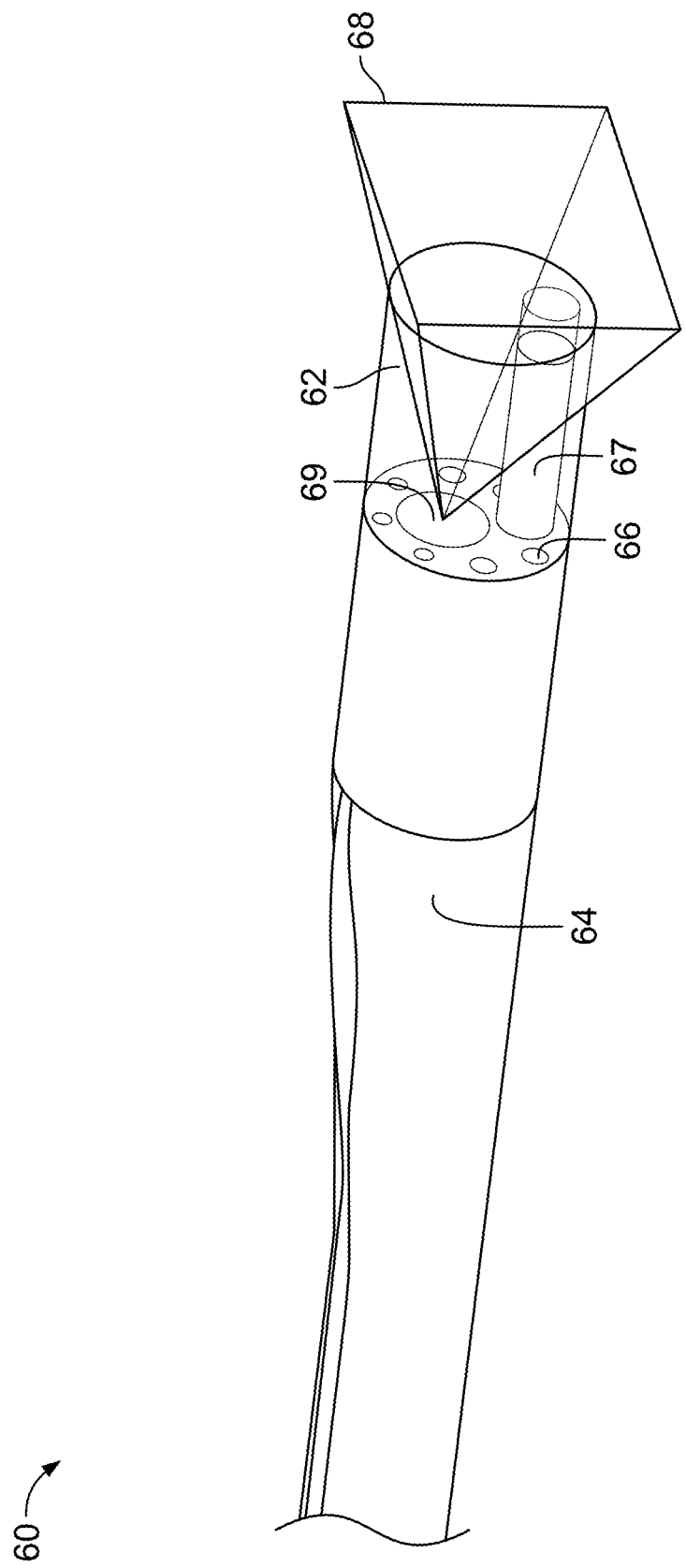

In the example of FIG. 6, a cardioscope 60 including an optical window 62 is mounted on a structural component 64. The structural component 64 includes holes 66 allowing the silicone of the optical window 62 to penetrate therein, thus stabilizing the optical window 62 on the structural component. The field of view 68 of a camera 69 is unobstructed due to the placement of a tube 67 in the proximal portion of a tool channel 65. The assembly of the cardioscope 60 can be seen in FIGS. 7A-7C.

In some examples, the optical window 110 is formed by molding. A mold, for instance a polymer mold, of the optical window 110, including the tool channel 120, the flushing channel 130, and a hollow for the camera 112 and illumination device, can be created, for instance, by three-dimensional printing, injection molding, extrusion, or other molding processes. The material of the optical window 110 is a transparent and optically clear polymeric material, e.g., silicone or silicone rubber (e.g., QSil 216 or QSil 218, Quantum Silicones), is cast into the mold and allowed to cure. In some cases the optical window 110 is mounted on a structural component, which can be created, for instance, by three-dimensional printing, injection molding, or other processes.

Geometry of the Optical Window

The geometry of the optical window 110 can enable the camera 112 to achieve a large field of view of the tissue, for instance, enabling visualization of tissue before, during, and after a procedure, and enabling visualization of the position and depth of the tool relative to the tissue before, during, and after the procedure. In addition, the geometry of the optical window 110 can facilitate operation of the tool, for instance, by providing a suitable angle of contact between the tool and the tissue or by accommodating an angle of approach for the tool that is suitable for a given procedure. In some examples, an angle of contact between the tool and the surface normal of the tissue is less than 90°, e.g., about 45°.

The geometry of the optical window 110 can depend on where the instrument 100 is to be deployed, the nature of the tool to be used with the instrument, or both. For instance, a target angle of approach for a tissue removal tool may be different than a target angle of approach for a catheter, and a dedicated optical window 110 with a geometry to achieve the appropriate angle of approach may be designed for each tool.

The geometry of the optical window 110 can depend on the wavelength of light provided by the illumination source. For instance, the index of refraction of the material of the optical window (e.g., silicone or silicone rubber) and of the blood can vary based on the wavelength. The geometry of the optical window 110 can thus be specific to the wavelength of light, such as visible light or infrared light, in order to, e.g., enable the camera 112 to achieve a large field of view. Because blood is transparent to infrared wavelengths, imaging with infrared light can enable visualization of structures ahead of the distal face of the optical window even in the presence of blood. For instance, imaging with infrared light can enable a user to navigate a catheter through a blood-filled heart while avoiding coming near sensitive structures of the heart.

Referring to FIG. 8A, in some examples, the optical window 110 has a convex, hemispherical distal face 118a. A hemispherical distal face 118a can facilitate the displacement of blood the interface between the distal face 118a and tissue during tissue contact. A circular field of view can be achieved by pressing the hemispherical distal face 118a into tissue. In addition, with a hemispherical distal face 118a, the tool 300 can be positioned off center, for instance, to achieve an angle of tool-tissue contact of less than 90°, such as an angle of about 45°. Referring to FIG. 8B, in some examples, the optical window 110 has a convex distal face 118b, e.g., with surface curvature in only a single axis or in multiple axes. In some examples, the optical window has a concave distal face (not shown).

Referring to FIG. 8C, in some examples, the optical window 110 has a planar distal face 118c. The planar distal face 118c provides a large field of view at low contact force with the tissue and can effectively evacuate blood from in front of the distal face 118c when in contact with tissue. The planar distal face 118c also enables the tool 300 to be positioned within the field of view of the camera 112 and allows the tool 300 to be angled to achieve a desired angle of approach.

Referring to FIG. 8D, in some examples, the optical window 110 has a distal face 118d with an angled planar surface. An angled planar surface is a surface whose normal is disposed at an angle greater than 0° relative to a longitudinal axis of the optical window 110. The angled planar distal face 118d provides a large field of view at low contact force with the tissue and can effectively evacuate blood from in front of the distal face 118d when in contact with tissue. The angled planar distal face 118d also enables the tool 300 to be positioned within the field of view of the camera 112 and allows the tool 300 to be positioned to achieve a desired angle of approach. In addition, with the angled planar distal face 118d, a desired angle of tool-tissue contact can be achieved. In some examples, the angled planar distal face 118d can be angled such that the normal to the distal face 118d is at an angle Φ of between about 20-25° from the longitudinal axis of the optical window 110, such as an angle of about 20°, about 21°, about 22°, about 23°, about 24°, about 25°, or another angle. Selection of an appropriate angle Φ, for instance, based on anatomy in the target region of the heart, can enable contact to be achieved between the angled planar distal face 118d and the tissue over the entire target region.

The diameter of the optical window 110 can taper from a large diameter $d_1$ to a smaller diameter $d_2$ within a distal region 304 of the optical window 110. The large diameter $d_1$ can be, for instance, between about 1 mm and about 20 mm, or between about 3 mm and about 6 mm, e.g., about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, or another diameter. The smaller diameter $d_2$ can be, for instance, between about 2 mm and about 15 mm, e.g., about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, or another diameter. A proximal region 306 of the optical window 110 having a constant diameter $d_1$ can extend from the end of the distal region 304 to the proximal end of the optical window 112. For instance, the optical window 110 can have the large diameter $d_1$ at the position where the optical window 110 passes through the heart wall. The camera 112 can be positioned within the large diameter proximal region 306, enabling a large field of view to be achieved. The smaller diameter at the distal end of the optical window 110 allows the distal face 118 of the optical window 110 to slide smoothly over tissue with little trapping of blood between the tissue and the distal face 110.

In some examples, the tool channel 120 is positioned in the center of the optical window 110. In some examples, the tool channel 120 is offset relative to the center of the optical window 110. The tool channel 120 can be aligned with the optical window 110 or can be positioned at an angle relative to the longitudinal axis of the optical window 110. For instance, an angle θ between the longitudinal axis of the tool channel 120 and the longitudinal axis of the optical window 110 can be between about 0° and about 90°, e.g., about 0°, about 5°, about 10°, about 15°, about 20°, about 25°, about 30°, about 35°, about 40°, about 45°, about 50°, about 55°, about 60°, about 65°, about 70°, about 75°, about 80°, about 85°, about 90°, or another angle. The tool channel 120 can be positioned at an angle to the camera 112, e.g., to enable visualization of a desired field of view. For instance, an angle α between the longitudinal axis of the camera 112 and the longitudinal axis of the tool channel 120 can be between about 0° and about 30°, e.g., about 0°, about 5°, about 8°, about 10°, about 15°, about 20°, about 25°, about 30°, or another angle. The positioning of the tool channel 120 within the optical window 110 determines the angle of contact between the tool 300 and the tissue. The angle of contact β between the tool and the surface normal of the tissue can be less than 90°, e.g., about 0°, about 10°, about 20°, about 30°, about 40°, about 45°, about 50°, about 60°, about 70°, about 80°, about 85°, or another angle.

The positioning and orientation of the tool channel 120 within the optical window 110 can depend on, e.g., the type or size of the tool 300 to be inserted into the tool channel 120, the environment in which the tool 300 is intended to operate, or other factors. The placement of the tool channel 120 can also be selected to achieve a desired position of the distal tip of the tool 300 in the field of view of the camera 112. In an example, the tool 300 is a tissue removal tool (discussed further below) for removing tissue in corners under a heart valve, such as in the infundibulum below the pulmonary valve. To enable the distal tip of the tool 300 to reach into the narrow corners, the tool channel 120 can be positioned off center in the optical window 110. In addition, to enable visualization of the tissue cutting procedure and observation of the depth of the cut, the camera 112 and the tool channel 120 can be angled toward each other.

In the specific example of FIG. 8D, the tool 300 is a tissue removal tool. The large diameter $d_1$ of the optical window 110 is 14 mm. The camera 112 is rotated by 6° and the tool channel 120 is rotated by 2° to achieve an angle α between the camera 112 and the tool channel 120 of 8°. The angle Φ between the normal to the distal face 118d and the longitudinal axis of the optical window 110 is 22°. With this geometry, the angle of contact between the tool 300 and the surface normal of the tissue is 20° and the camera achieves a field of view of 7.5×10 mm.

Referring to FIGS. 9A and 9B, in some examples, multiple cameras or multiple tool channels can be positioned within the optical window, e.g., in order to achieve tool triangulation or multiple camera viewing angles. In the example of FIG. 9A, two cameras 112a, 112b are positioned within the optical window 110, thus providing a broad field of view in front of the distal face 118 of the optical window 110 and to the side of the optical window 110. In the example of FIG. 9B, two tool channels 120a, 120b are formed through the optical window and curved such that tools inserted through the tool channels 120a, 120b can work cooperatively at a single surgical site. The camera 112 in the example of FIG. 9B is positioned and angled such that the distal opening of each tool channel 120a, 120b and the meeting point of the tools inserted therethrough both fall within the field of view of the camera 112.

Uses of the Cardioscope with a Tissue Removal Tool

Figure 10:
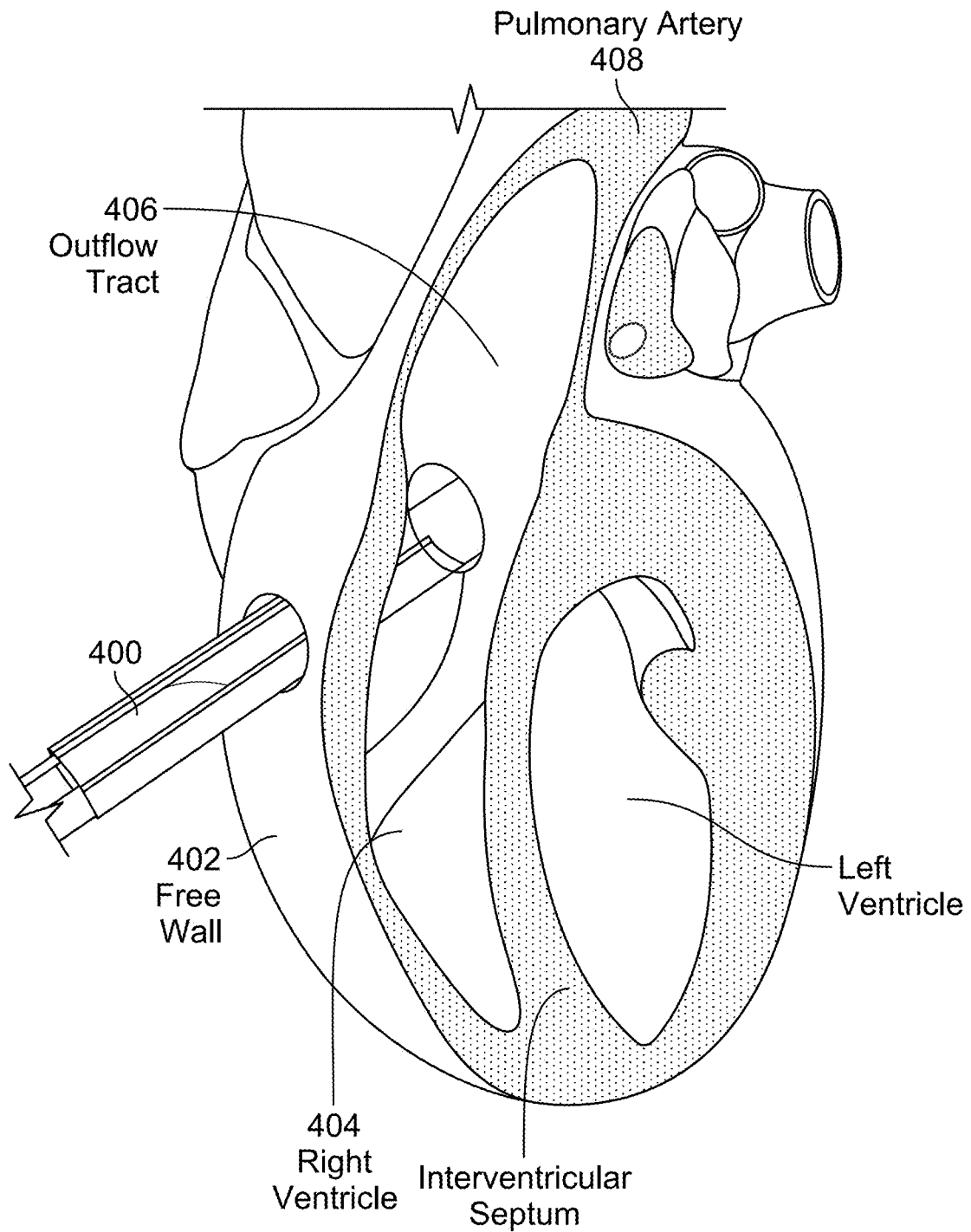
FIG. 10 is a schematic diagram of the interior of a heart illustrating placement of one of the devices described herein.

In some examples, the tool that is inserted through the tool channel 120 of the optical window 110 of the instrument 100 is a tissue removal tool. The tissue removal tool can be used to remove cardiac tissue from the interior of the heart to treat, e.g., congenital heart defects such as pulmonary stenosis. For instance, referring to FIG. 10, an instrument 400 including a tissue removal tool can be inserted through the free wall 402 of the right ventricle 404 and used to remove excess tissue in the outflow tract 406 below the pulmonary valve 408, in a region known as the infundibulum. Removal of excess tissue in the infundibulum can relieve obstruction of the valve or outflow tract from the right ventricle into the pulmonary artery to treat pulmonary stenosis. The optical window enables visualization of the positioning of the tissue removal tool before and during contact with the tissue in the infundibulum and enables real time imaging as the excess tissue is removed by the tissue removal tool.

Figure 11A:
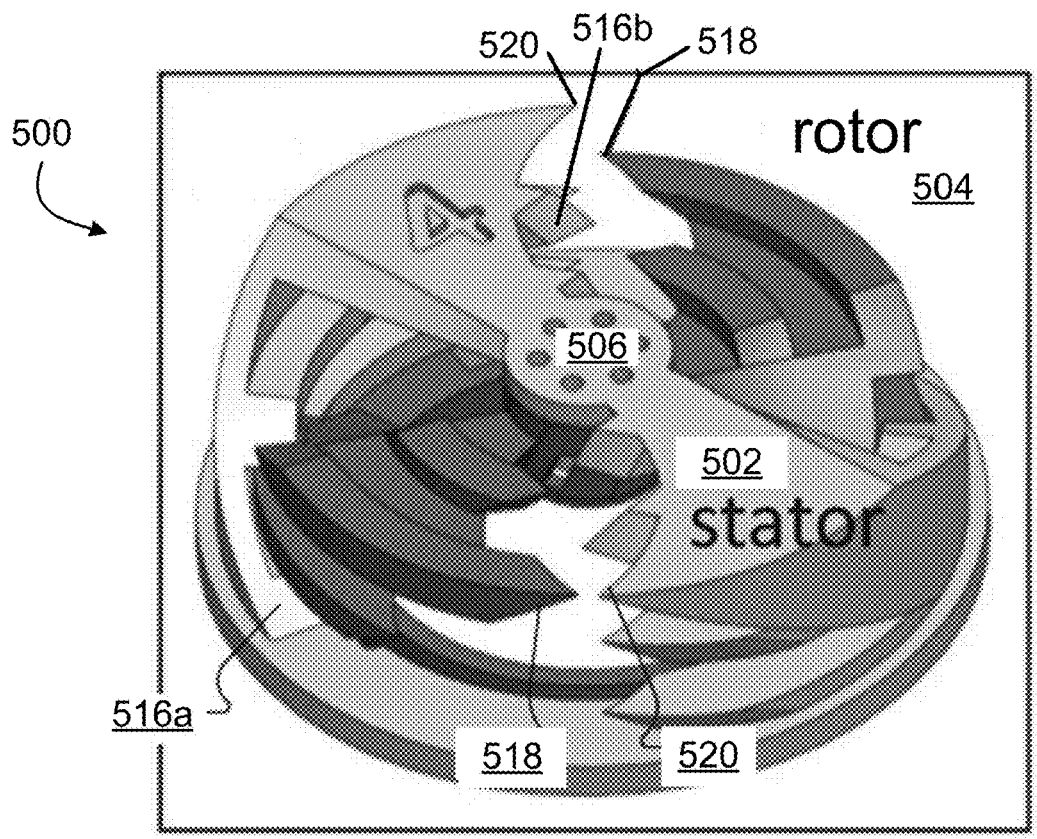
FIGS. 11A-11C are diagrams of a tissue removal tool as described herein.
Figure 11B:
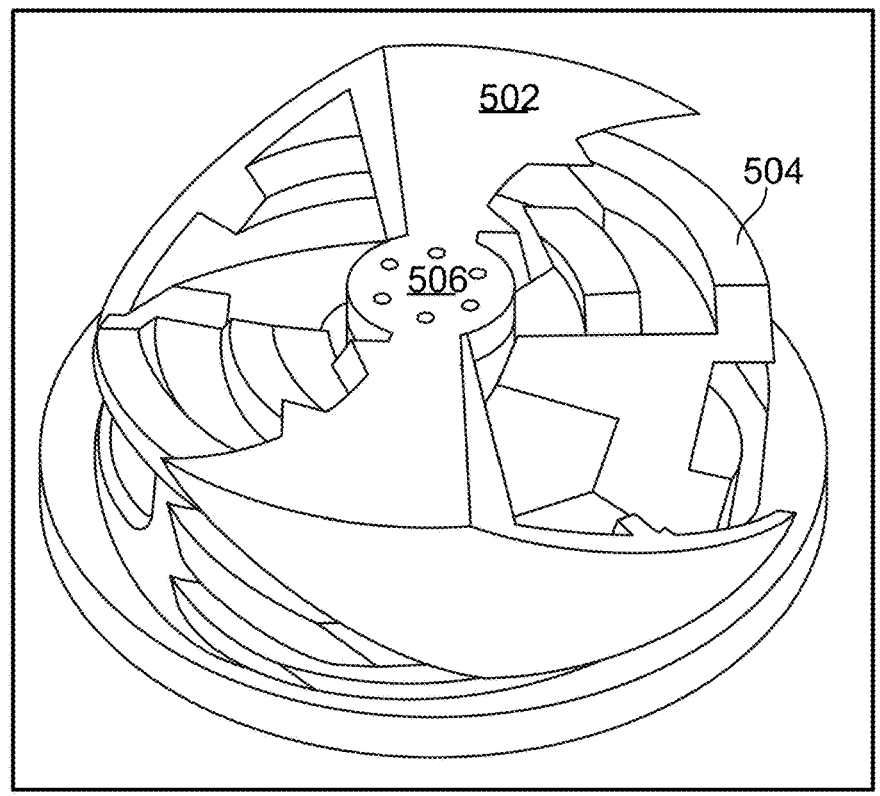
Figure 11C:
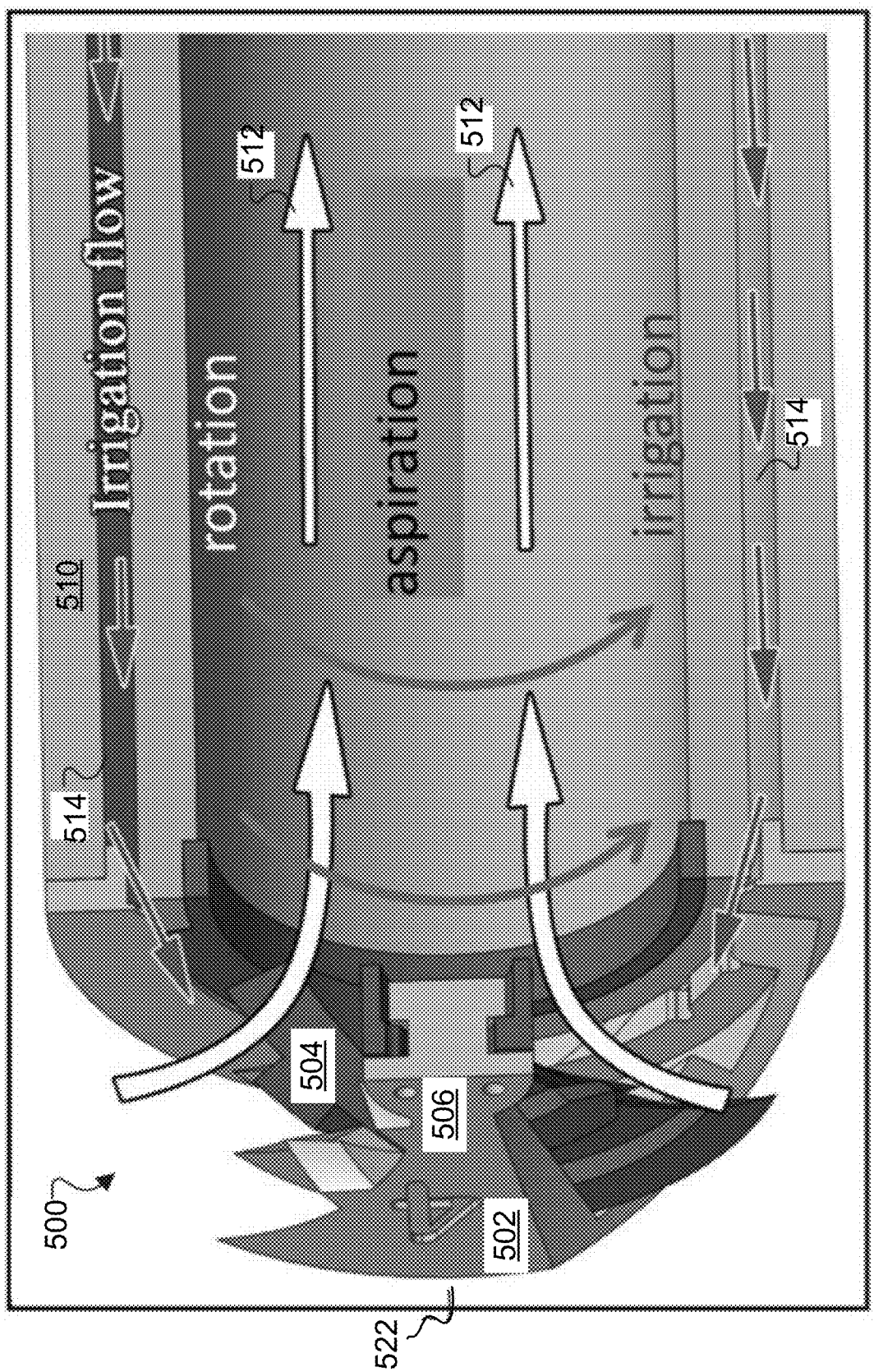

Referring to FIGS. 11A-11C, an example of a tissue removal tool 500 has a diameter of 2 mm, although tissue removal tools with other dimensions are also possible. The tissue removal tool 500 includes a stator 502 and a rotor 504 attached by an integrated bearing 506. The rotor 504 is attached to an inner rotating tube 508, e.g., by laser welding or another attachment technique. The rotating tube is driven by a motor, such as a motor 138 shown in FIG. 1. The stator is attached to a stationary outer tube 510, e.g., by a snap fit connection or another attachment technique. A vacuum pump (not shown) is used to aspirate tissue debris through the hollow central channel of the rotating tube 508, as shown by arrows 512. To avoid clogging of the tissue removal tool 500 and to reduce blood loss, the cutting interface can be irrigated, e.g., with heparinized saline, provided through a gap 514 between the outer surface of the rotating tube 508 and the inner surface of the stationary outer tube 510.

The stator 502 in this example includes two cutting windows 516a, 516b. Efficient tissue removal occurs when the tissue removal tool 500 is oriented such that tissue presses against one of the cutting windows 516a, 516b. Teeth 518 of the rotor 504 mesh with teeth 520 of the stator 502 to slice the tissue. Debris is transported away from the cutting interface through the hollow central channel of the rotating tube 508.

The tissue removal tool 500 is operated by sliding a distal tip 522 of the tissue removal tool 500 across the tissue at an angle of less than 90° between the axis of the tissue removal tool 500 and the plane of the tissue surface. For instance, the tissue removal tool 500 can be held at a 45° angle to the tissue surface. By inserting the tissue removal tool 500 into the optical window 110 as described above, the angle between the tissue removal tool 500 and the tissue surface can be controlled such that a desired angle is achieved.

During tissue removal, the depth of the cut by the tissue removal tool 500 during each of a series of passes over the tissue can be limited to avoid gouging the tissue or damaging the tissue removal tool 500. Heart tissue motion over the cardiac cycle varies by location, but can be up to a centimeter. Consequently, the depth of the cut into cardiac tissue cannot be accurately controlled simply by rigid positioning of the tissue removal tool. Integration of the tissue removal tool 500 into the optical window 110 enables precise control of the cutting depth even in situations where the tissue is not stationary, such as in a beating heart. The distal face 118 of the optical window 110 acts as a depth control device, e.g., similar to a sole plate of a woodworking router. The distal face 118 of the optical window 110 is pressed against the tissue to establish stable contact between the optical window and the tissue. The distal tip of the tissue removal tool 500 is extended out from the distal face 118 of the optical window 110 by a specific and controlled amount. The optical window 110 maintains continuous contact with tissue 500 even as the tissue moves, e.g., even as the heart beats, thus keeping the depth of the cut stabilized at a constant value. For instance, by pressing lightly into the tissue, contact can be maintained over the cardiac cycle. The contact force will vary over the cardiac cycle, but is small enough to not cause any damage, in part because the contact force is applied over the compliant surface of the optical window 110. If the tool is rigid, such as in the case of the instrument 100, the tissue is locally immobilized. When the cardioscope is used at the distal tip of a flexible instrument, such as a catheter, the instrument flexes over the cardiac cycle.

In some examples, one or more marks can be made on the tool (e.g., the tissue removal tool 500) to enable a viewer of an image to determine the depth of penetration of the tool into the tissue.

Referring also to FIG. 1, the extension of the distal tip 522 of the tissue removal tool 500 can be controlled by a trigger 142 in the handle 116 of the instrument 100. To achieve a tool extension resolution of a fraction of a millimeter, the trigger 142 is operable in an on-off fashion. When the trigger 142 is pulled, the distal tip 522 of the tissue removal tool 500 is retracted into the optical window 110. When the trigger 142 is released, a spring extends the distal tip 522 of the tissue removal tool by a discrete distance. In some examples, the discrete distance by which the distal tip 522 is advanced each time the trigger 142 is released can be set, e.g., digitally or mechanically, such as by an adjusting screw. The trigger 142 can be sufficiently responsive and the handle 116 sufficiently lightweight to allow a user to operate the instrument 100 with just one hand. Once contact is established between the tool and the tissue, the trigger 142 allows for extension of the tool relative to the instrument (e.g., the instrument 100). In some examples, trigger release causes tool extension and pulling the trigger retracts the tool. In some examples, trigger release retracts the tool and pulling the trigger causes tool extension.

In some examples, the tissue removal tool 500 can be fabricated using a metal MEMS (microelectromechanical system) fabrication process in which 25 μm thick layers of structural metal, such as NiCo, and sacrificial metal, such as copper, are deposited by photolithographic electrodeposition. In some examples, the handle 116 can be fabricated by molding, three-dimensional printing, or another fabrication process. The handle 116 can be made of a lightweight, rigid, biocompatible plastic such as acrylonitrile butadiene styrene (ABS) plastic. In some embodiments, the tool and optical window are designed to be disposable. In some embodiments, the tool is designed to be sterilized and reused with only the optical window being disposable. In some embodiments, the tool and optical window are both designed to be sterilized and reused. The optical window can be easily sterilized when the design of the optical window is such that the components of the optical window are encapsulated therein and the optical window is formed of a material with high temperature tolerance, such as silicone. The handle can be made disposable or reusable.

Figure 12:
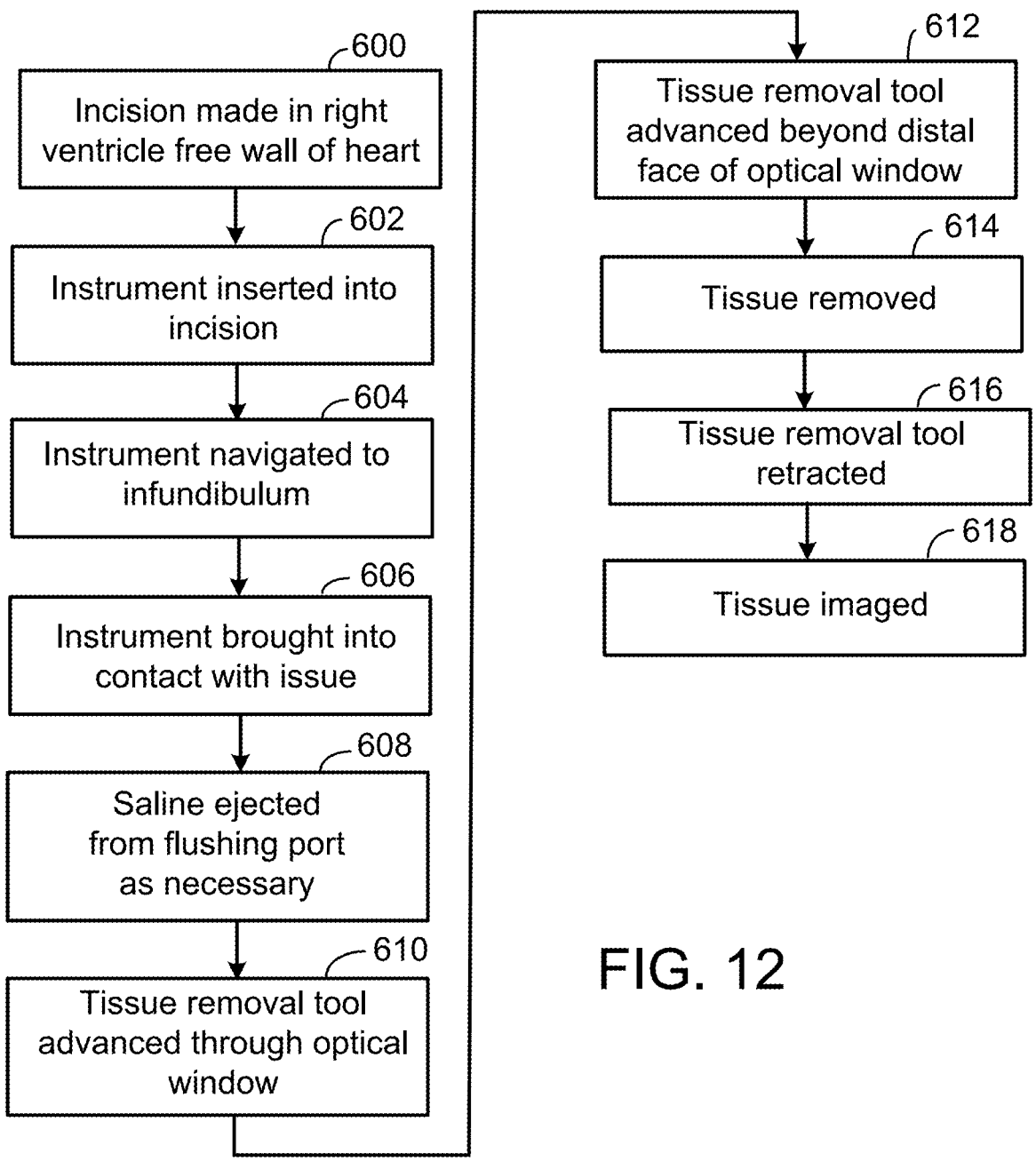
FIG. 12 is a flow chart of a procedure for using an optical window with a tissue removal tool.

Referring to FIG. 12, in an example of a procedure for using an optical window with a tissue removal tool, an incision is made in the right ventricular free wall of the heart (600). An instrument including an optical window at its distal end is inserted through the incision (602) and navigated to the infundibulum via image guidance from the camera in the optical window (604). For instance, imaging can indicate the closeness of the distal tip of the optical window to the target tissue and can indicate when contact has been made between the optical window and the target tissue. The instrument is brought into contact with the tissue at the target location (606), guided by imaging from the optical window. During the positioning, saline can be ejected from the flushing port (608) as necessary to provide a clear view, such as to provide a temporary view of the anatomy of the tissue prior to contact or to clear any trapped blood after contact.

When the optical window is positioned at the desired location on the target tissue, a tissue removal tool is advanced through the instrument channel of the optical window (610). While the tissue removal tool can be advanced prior to positioning of the optical window, the tissue removal tool would partially occlude the field of view of the camera in the optical window, thus making positioning of the optical window more challenging. The tissue removal tool is further advanced beyond the distal face of the optical window (612) into the tissue and tissue is removed as appropriate (614). The cutting depth of the tissue removal tool during tissue removal is controlled by the contact between the distal face of the optical window and the tissue such that, even as the heart tissue moves throughout the cardiac cycle, the cuts by the tissue removal tool remain at a constant depth.

When the procedure is finished, the tissue removal tool is retracted out of the optical window (616) so as not to block the field of view, and images are acquired of the tissue following the procedure, if desired (618). Post-procedure images can be used, for instance, to confirm that the procedure has been completed correctly, to monitor for abnormal bleeding, or for other purposes.

Uses of the Cardioscope with a Catheter

Cardioscopes can be used to provide image guidance and positioning and depth control for various catheter-based beating heart procedures, e.g., valve repair or replacement, closure of openings between the two atria of the heart, tissue removal, tissue ablation, the placement or removal of various diagnostic or therapeutic devices, biopsy, local injection, in situ imaging such as ultrasonic, infrared, or optical coherence tomography (OCT) imaging, or other procedures. The dimensions and geometry of the optical windows can vary based on characteristics of the device and metrics of the procedure. For instance, a larger version of an optical window can be disposed at the distal tip of an ablation catheter having a diameter of about 5-6 mm.

Figure 13:
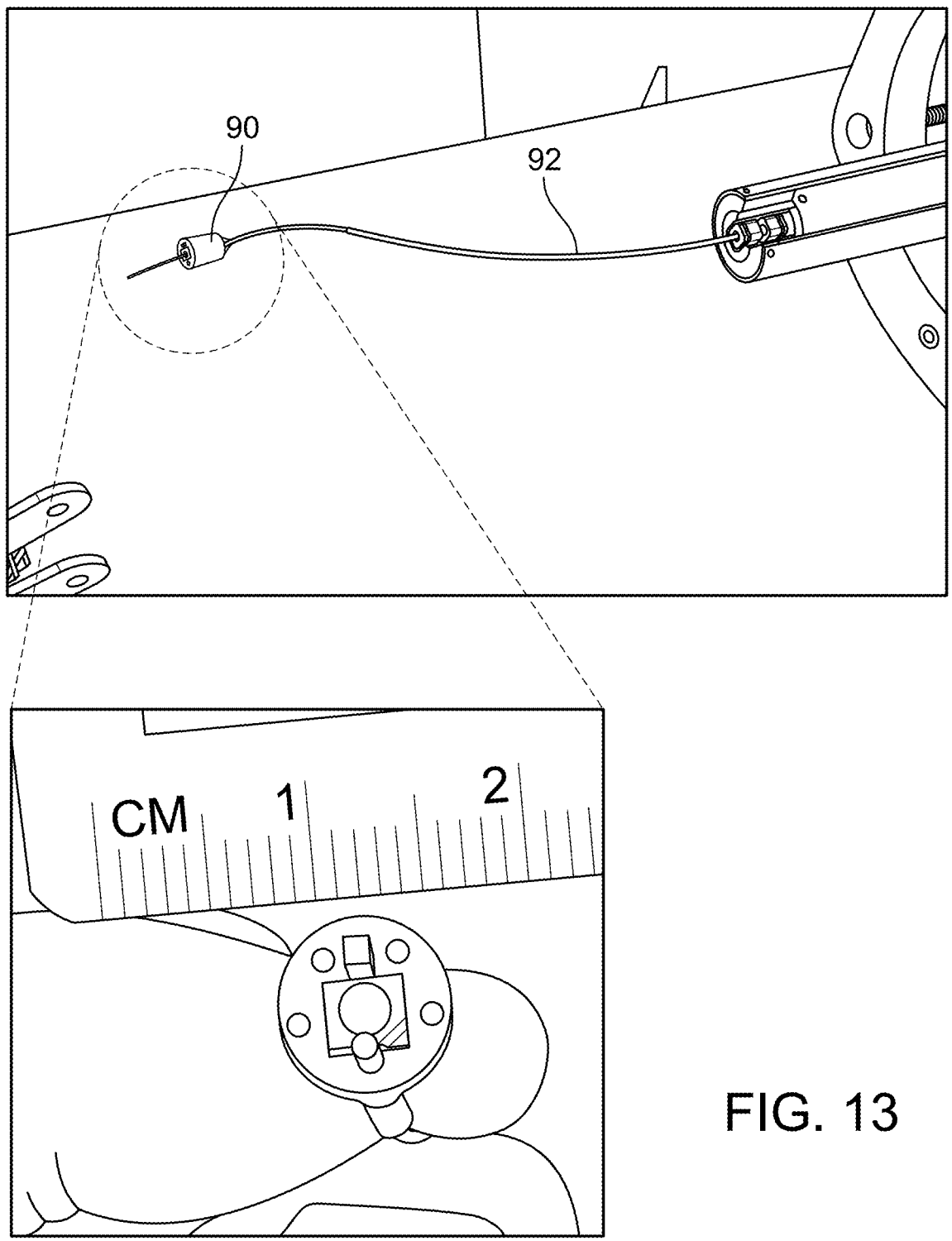
FIG. 13 is a photograph of a cardioscope.

Referring to FIG. 13, a cardioscope 90 is provided at the distal tip of a robotic catheter 92 to provide imaging capabilities for guiding the navigation and positioning of the catheter and for guiding and controlling the operation of a tool inserted through the tool channel of the cardioscope 90.

Figure 14:
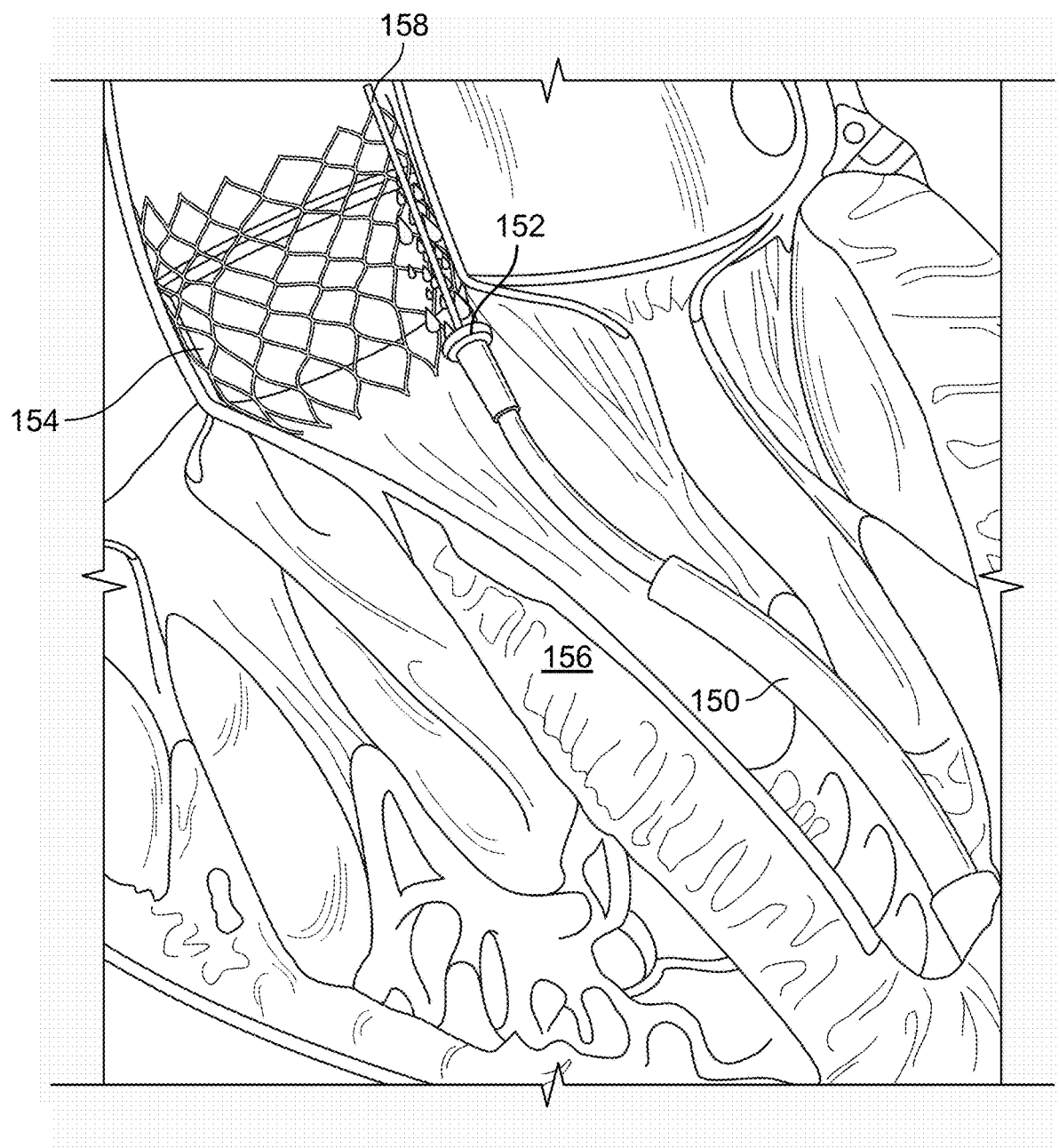
FIG. 14 is a diagram of a catheter with a distal cardioscope for repairing a paravalvular leak.

Referring to FIG. 14, in some examples, a catheter 150 with a distal cardioscope 152 can be used for the detection and repair of leaks around a replacement valve 154 in a heart 156, such as an aortic paravalvular leak (PVL). The catheter 150, including the distal cardioscope 152, is inserted into the heart 156 through an introducer sheath (not shown) placed through the apex of the heart and navigated through the left ventricle and to the periphery of the aortic annulus. The optical window of the cardioscope 152 enables visualization of the positioning of the distal tip of the catheter relative to the valve 154 and possibly visualization of the leak itself. For each PVL, a wire 158 is passed through the leak and an occluder device (not shown), such as an Amplatzer® ductal or vascular occluder, is deployed along the wire 158 to repair the PVL. The distal cardioscope 152 enables the catheter 150 to be precisely positioned at the area of the leak, enables visualization of the replacement valve and the surrounding tissue, and enables visualization and control of the placement of the wire and the occlude device. The visualization and control provided by the distal cardioscope 152 enables the PVL repair procedure to take place in a beating heart.

In some examples, cardioscopes as described herein can be deployed to help in identification of the location of a PVL. A bolus of saline, much smaller than the field of view of the camera in the optical window, can be ejected from the flushing channel of the optical window into the space between the distal face of the optical window and the tissue. If there is no leak, the bolus of saline dissipates uniformly in front of the distal face of the optical window. If, however, a leak is nearby, the bolus of saline is rapidly and non-uniformly dispersed away from the source of the leak. The dispersal of the bolus of saline can be visualized and used to determine the likely location of a PVL, as well as to qualitatively or quantitatively characterize blood flow patterns in the heart. In some examples, a bolus of a colored material, such as methylene blue, can be ejected from the flushing channel in order to assist with visualization of blood flow patterns.

In another example, of the catheter 150 is an ablation catheter and the cardioscope 152 provides image guidance, visualization of the ablation site, and control of the depth of the catheter tip.

Figure 15:
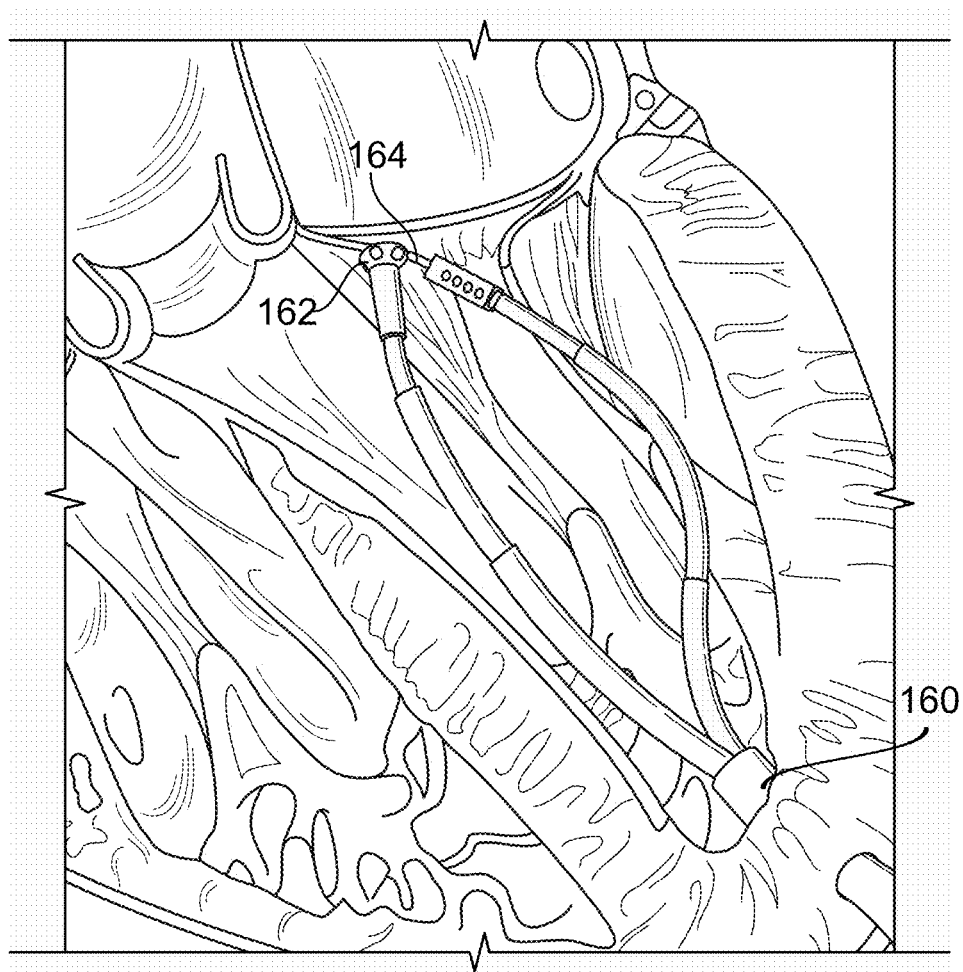
FIG. 15 is a diagram of a catheter with a distal cardioscope for manipulation of a mitral leaflet.

Referring to FIG. 15, in another example, a catheter 160 with a distal cardioscope 162 can be used for image-guided manipulation of a mitral leaflet 164. In the example of FIG. 15, the catheter 160 is a two-handed robotic catheter enabling bimanual tissue manipulation. In some examples, the catheter 162 can be a single branch catheter.

Figure 16A:
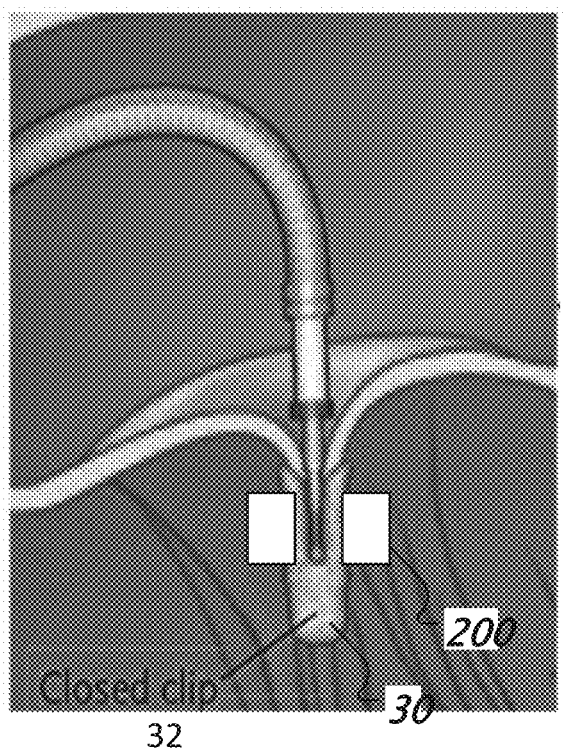
FIGS. 16A and 16B are diagrams of a mitral valve clip and a tissue gripping device, respectively, with a distal cardioscope.
Figure 16B:
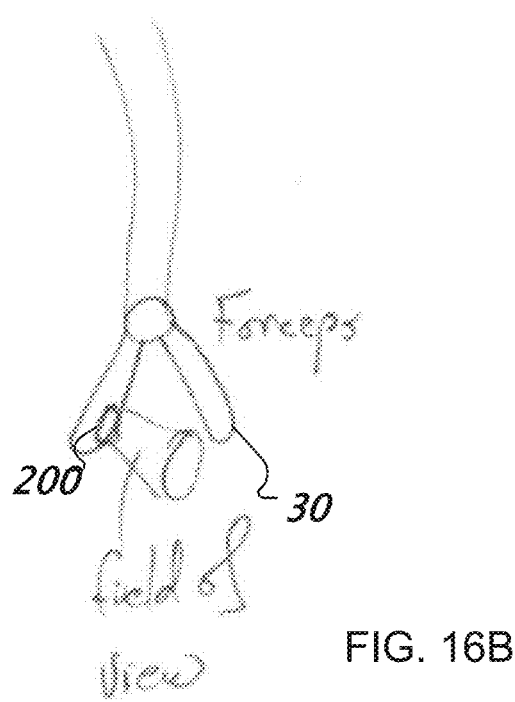

Referring to FIGS. 16A and 16B, in another example, a cardioscope 200 is integrated with a mitral valve clip 32, and a tissue gripping device 30, or both, to enable image-guided valve repair. In cardiac valve repair, a tissue gripping device such as the tissue gripping device 30 is used to grip the valve leaflet, and the tissue gripping device 30 is then moved along the leaflet to the repair location. At the repair location, a clip such as the mitral valve clip 32 can be placed or a suture inserted to repair damage to the leaflet. With cardioscopic imaging integrated into the tissue gripping device 30, the positioning of the tissue gripping device 30 on the valve leaflet can be visualized and the tissue gripping device 30 can be precisely moved to the repair location. The damage to the leaflet can also be visualized. Cardioscopic imaging integrated into the mitral valve clip 32 can enable precise positioning of the mitral valve clip 32 and subsequent visual monitoring of the healing progress of the leaflet, e.g., to view how much and what tissue is grasped.

Figure 17:
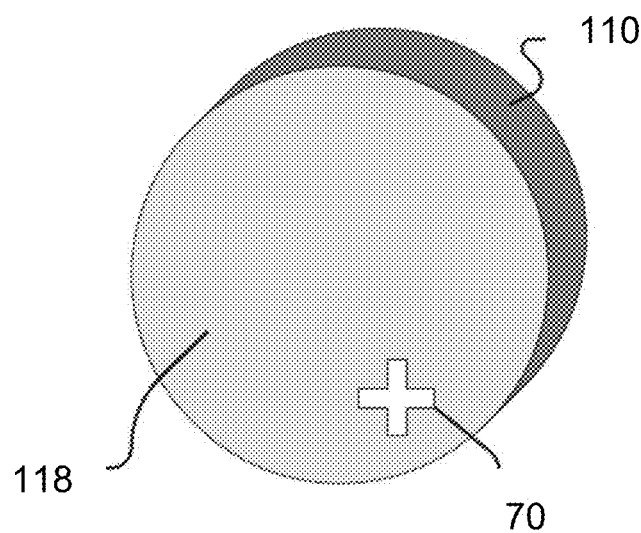
FIG. 17 is a diagram of an optical window with a fiducial marking.

Referring to FIG. 17, in some examples, the distal face 118 of the optical window 110 can be marked with one or more fiducial markings 70 that can be used to measure distances on tissue, such as the diameter of a PVL, the distance from the tip of a tissue gripping device to the edge of a leaflet, the size of an area of removed tissue, or other distances of interest.

In some examples, no fiducial markings are used. The camera images can be calibrated for the field of view through the distal face and precise dimension measurements can be performed during or after surgery using the images. For instance, a ruler or grid can be overlaid on the digital image to perform a measurement visually, or an automated measurement approach can be used. An operator, such as a surgeon or an analyst, can manually or automatically process the image, for instance by drawing a line or rastering the image, to record information during or after surgery. The images can be recorded in a standard format, such as a dicom format, to facilitate post processing of the images.

Alternative Optical Window Structures

Figure 18:
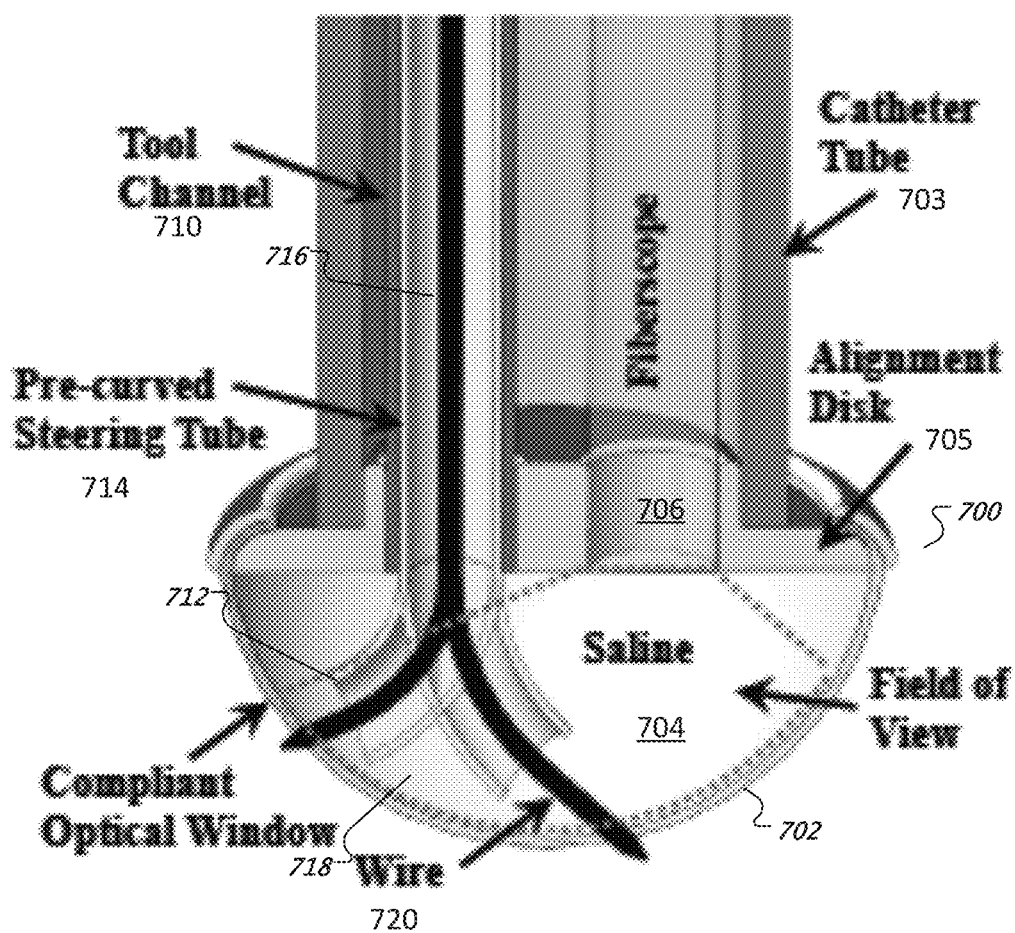
FIG. 18 is a diagram of an alternative example of an optical window.

Referring to FIG. 18, an alternative optical window 700 includes a transparent, compliant, hollow polymer bulb 702 that is curved, such as into a hemispherical shape. For instance, the bulb 702 can be formed of silicone (e.g., available from NuSil Technology), silicone rubber, or another transparent, compliant, biocompatible polymer. The compliance of the bulb 702 can be controlled by the thickness and composition of the polymer and the conditions under which the polymer is processed, such as the curing temperature. The compliance of the bulb 702 allows the bulb 702 to conform to irregular surfaces, thus effectively displacing blood from between the outer surface of the bulb 702 and the tissue. An interior 704 of the bulb 702 is filled with a clear, biocompatible liquid, such as saline.

The bulb 702 is disposed at a distal end of a device 703, such as a catheter or instrument port. The device 703 includes optical components, such as a camera, a camera on a chip, an optical fiber 706, or an illumination device, and a tool channel 710 to receive a tool. The tool channel 710 can be a structurally robust tube, such as a polyimide tube reinforced with wire braiding, to support the passage of pre-curved tubes and wires therethrough, as described below. In some examples, the optical components, the tool channel 710, or both, can be glued to the interior of the device 703, for instance using medical grade epoxy. An alignment disk 705 connects the bulb 702 to the device 703 and acts as a structural and watertight connection between the interior of the device 703 and the interior 704 of the bulb 702. The alignment disk 705 can include holes for mating with the distal ends of the tool channel 710 and the optical fiber 706.

When the optical components of the device 703 include an optical fiber, the distal end of the optical fiber 706, which can include, for instance, a lens assembly, is exposed to the fluid-filled interior 704 of the bulb 702. In some examples, the optical fiber 706 can be press fit into the corresponding hole in the alignment disk 705 through one or more gaskets to provide a seal between the optical fiber 706 and the alignment disk 705. In some examples, a collar (not shown) can be attached to the distal end of the optical fiber 706, for instance, by gluing with a medical grade epoxy. The collar can be attached to the alignment disk 705 with fasteners to provide a structurally robust connection between the optical fiber 706 and the alignment disk 705.

The tool channel 710 in the device 703 does not extend into the interior 704 of the bulb 702. Thus, the field of view of the optical fiber 706 is unobstructed prior to introduction of a tool or other component through the tool channel and into the interior 704 of the bulb 702. A tool or other component inserted through the tool channel 710 can be steered to a desired contact point on the bulb 702, e.g., based on a position of the bulb relative to a target region of tissue. The tool can then pierce the bulb at the contact point and exit the bulb 702, contacting the target region of tissue. When the tool is later retracted inside the bulb 702, the hole in the bulb will seal itself due to the compliance of the polymer forming the bulb 702. A small flow rate of saline or other clear, biocompatible liquid, can be used subsequent to piercing of the bulb 702 or retraction of the tool to flush out any blood that penetrated to the interior of the bulb 702. In some examples, a tool can pierce the bulb at each of multiple contact points, the hole at each contact point sealing when the tool is retracted. The ability to steer a tool within the bulb 702 and to cause a tool to exit the bulb 702 at multiple contact points can reduce or eliminate the sliding of the bulb 702 along the tissue to achieve alignment between the tool and the target region of tissue. For instance, the tool can exit the bulb 702 at a first contact point to perform a procedure at a first location within the heart, then be retracted within the bulb 702 and exit the bulb 702 again at a second location to perform a procedure at a second, nearby location within the heart.

In some examples, a pre-curved steering tube 714 can be used to guide the tool within the interior of the bulb 702, e.g., to achieve alignment with a target region of tissue. The tube 714 can be a thin-walled metal or polymer tube, such as a NiTi or stainless steel tube, inserted through the tool channel 710 of the device 703. A proximal length 716 of the tube 714 is straight. A distal length 718 of the tube (e.g., the distal 5 mm) is pre-curved, such as the distal region of the tube extending beyond the alignment disk 705. When a tool is inserted through the tube 714, the tool will be guided to a position along the bulb 702 at which the curved distal length 718 of the tube 714 points. The tube 714 can be rotated within the tool channel 710 to point at a desired point on the bulb 702. For instance, FIG. 18 shows the tube 714 curved to point toward a position near the center of the bulb 702. FIG. 18 also shows an alternate orientation 712 in which the tube 714 has been rotated to point toward a position near the edge of the bulb 702.

In some examples, for instance, to achieve more precise steering or a sharper curvature within the interior of the bulb 702, a guide wire 720, such as a pre-curved guide wire, can be inserted into the tube 714. The guide wire 720 can control more precisely the point at which a tool inserted through the tube 714 will contact the bulb 702. For instance, the guide wire 720 can be oriented to either enhance or reduce the off-axis angle of the curved distal length 718 of the tube 714. Once the guide wire 720 is positioned properly, the tool can be passed along the guide wire 720 to its point of exit from the bulb 702.

In one example, when locating a paravalvular leak (PVL), the tube 714 can be oriented to point in the general direction of the PVL, and the guide wire 720 can be advanced through the tube 714 and steered to the specific location of the PVL, using image guidance provided by the camera 706. An occlusion device delivery catheter can then be passed through the tube 714 and along the wire to close the PVL.

Figure 19:
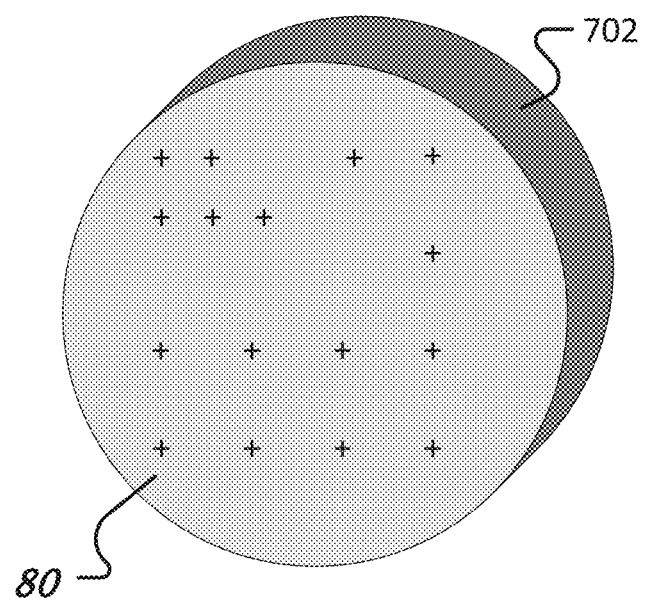
FIG. 19 is a diagram of an optical window with a pattern of crosshairs.

Referring to FIG. 19, in some examples, seals can be incorporated into the bulb 702 by partially or fully pre-cutting a pattern, such as a pattern of crosshairs 80, into the bulb 702. The presence of a pattern of crosshairs 80 can enhance tool steering within the bulb 702 to the set of discrete points designated by the pattern of crosshairs 80. The linear cuts of the crosshairs 80 can be self-sealing cracks that fold open to allow passage of a tool when the tool is pressed against the crack, and that re-seal when the tool is removed. The pre-cutting of a pattern of crosshairs 80 into the bulb 702 can help to address the situation in which the stiffness or tip geometry of the guide wire 720 or tool is insufficient to pierce the bulb 702. The pattern of crosshairs 80 can also serve as a set of fiducial distance markers.

In some examples, a small initial hole can be generated at the desired point on the bulb 702, for instance, using a radio frequency (RF) ablation wire, for instance, to help address the situation in which the stiffness or tip geometry of the guide wire 720 or tool is insufficient to pierce the bulb 702. In some examples, a seal can be constructed in the bulb 702 by pre-cutting larger crossed lines, similar to the seal in an introducer sheath, for instance, to help with the penetration of a tool too large to pierce the bulb 702. These same piercing and sealing features can be used in any of the compliant optical windows described herein.

Figure 20A:
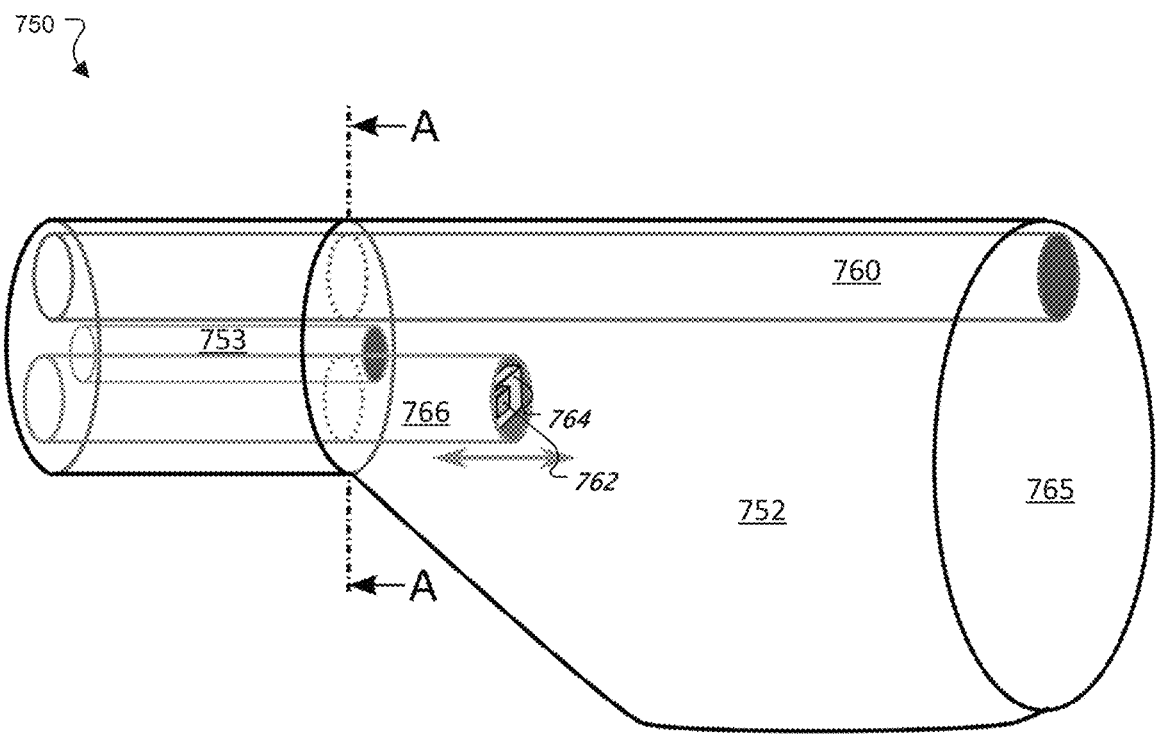
FIGS. 20A-20C and 21 are diagrams of an optical window with an expandable bulb.
Figure 20B:
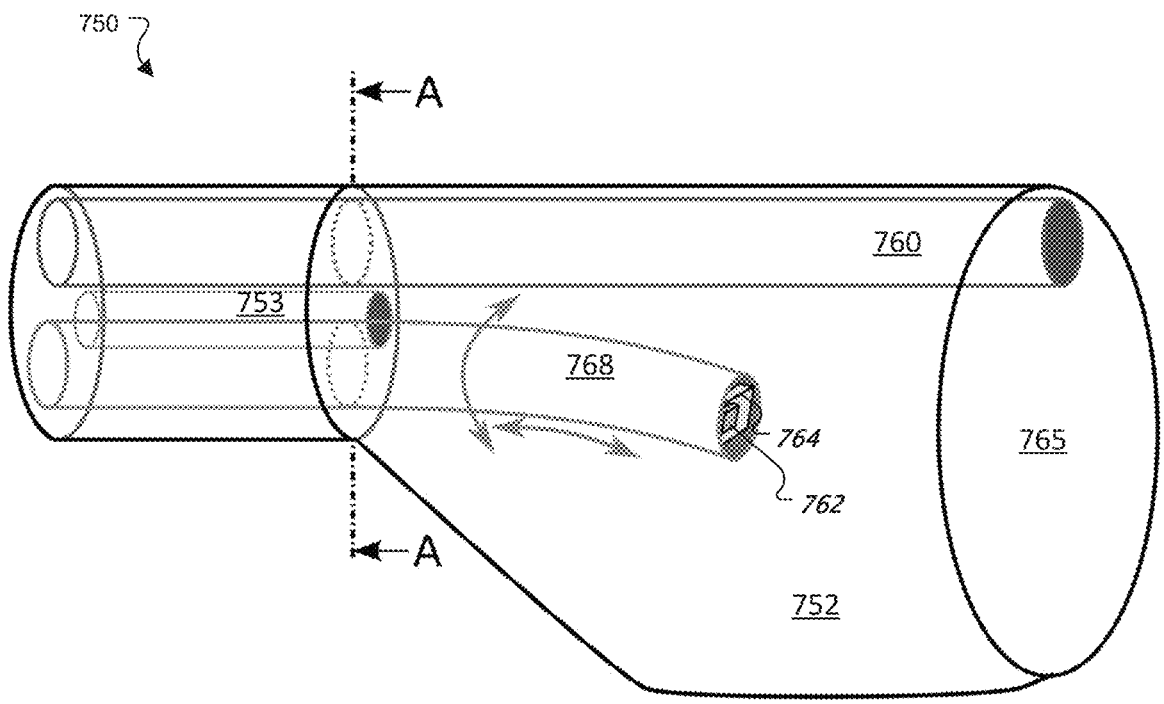
Figure 20C:
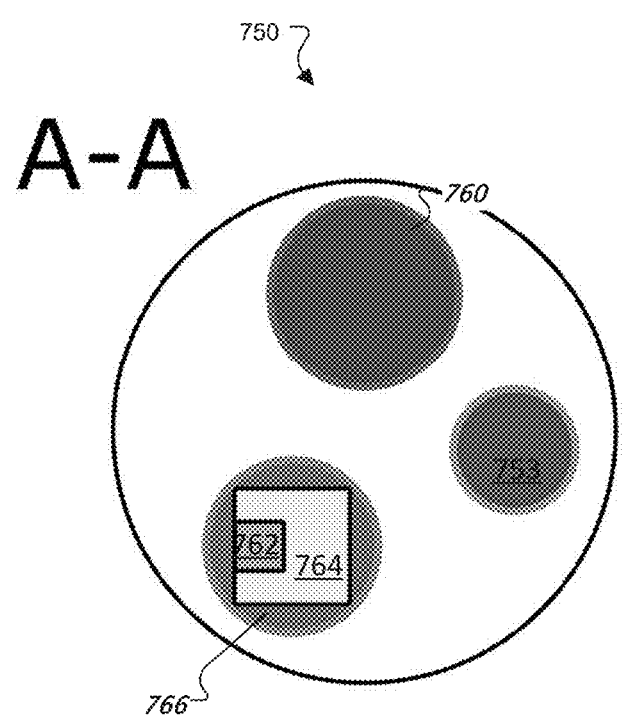

Referring to FIGS. 20A-20C, an alternative optical window 750 includes an expandable bulb 752 disposed at a distal end of a device, such as a catheter or an instrument port. Once the device is positioned at the procedure site, the expandable bulb 752 can be inflated, e.g., by filling the interior of the bulb 752 with a clear liquid such as saline or another clear, biocompatible liquid provided through a channel 753. In some examples, a continuous flow of liquid is not used with the expandable bulb 752.

An optically clear tube 760 forms a tool channel within the expandable bulb 752 through which a surgical tool can be inserted. The use of an optically clear tube to define the tool channel prevents the liquid filling the expandable bulb 752 from entering into the tool channel. A camera 762 and an illumination device 764 are positioned inside the expandable bulb 752 such that some or all of a distal face 765 of the expandable bulb 752 falls within the field of view of the camera 762.

In some examples, the camera 762 can be moveable within the expandable bulb 752. In some cases, as shown in FIG. 20A, the camera 762 can be located in a retractable tube 766 that can allow the camera to be positioned in a retracted position to allow a general view, e.g., of the surgical site, and to be advanced toward the distal face 765 of the expandable bulb 752 in order to enable high resolution imaging of specific areas of the surgical site. In some cases, as shown in FIG. 20B, the camera 762 can be disposed inside a curved tube 768, such as a nickel titanium (NiTi) tube, which can be rotated in order to enable the camera 752 to image different areas. In some examples, the illumination device 764 can be moveable within the expandable bulb 752. In some examples, the camera, the illumination device, or both can have a fixed position. For instance, the camera, the illumination device, or both can be inserted into and sealed within an optical channel formed within the expandable bulb 752.

Figure 21:
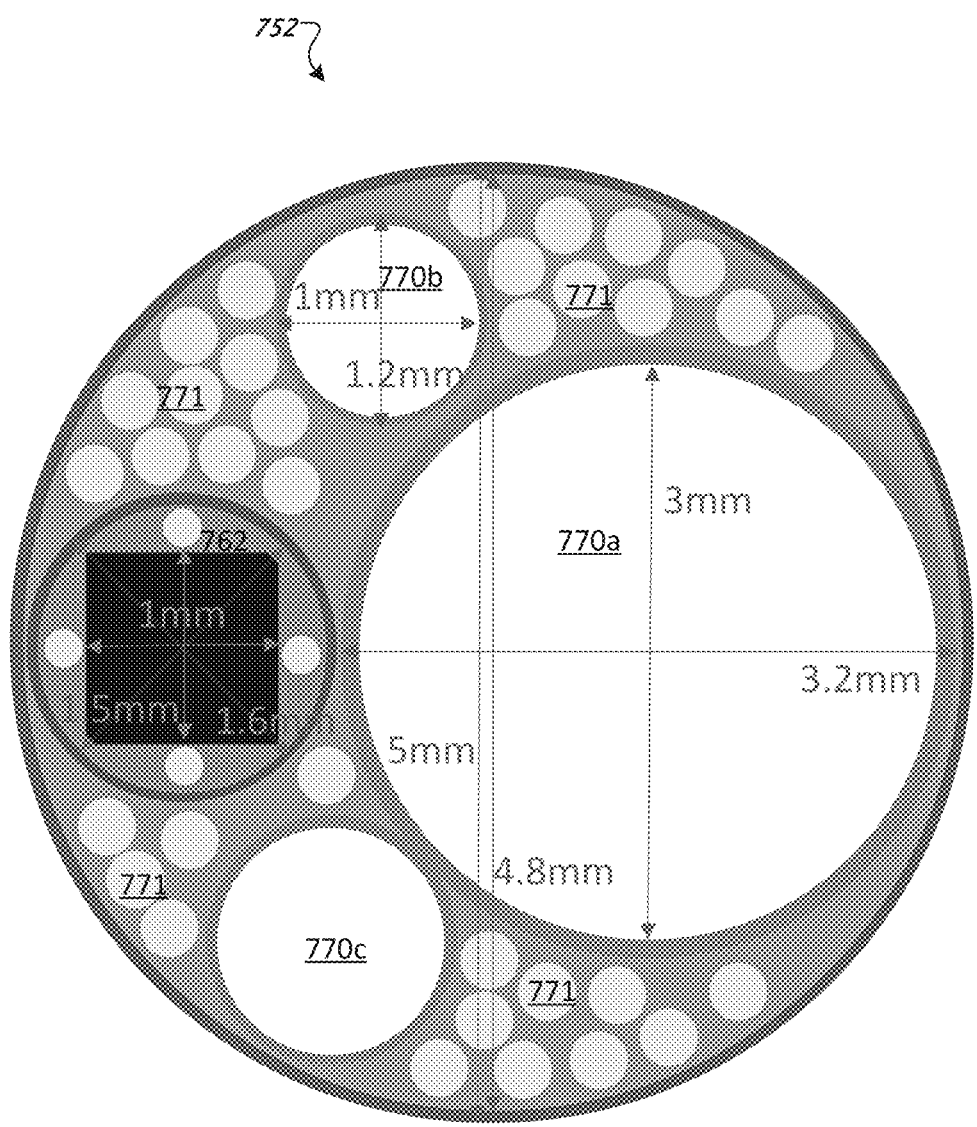

With the expandable bulb 752, the diameter of the device can be reduced, thus allowing the device to be used in applications for which a smaller device is appropriate. For instance, the outer diameter of the bulb 752 along the cross section A-A can be less than about 6 mm, such as about 4 mm, about 4.5 mm, about 5 mm, about 5.5 mm, or another diameter. The expandable portion of the bulb can expand to a diameter greater than about 8 mm, such as about 8 mm, about 9 mm, about 10 mm, or another diameter. Referring to FIG. 21, within this diameter, the expandable bulb can be sized to fit multiple channels and an imaging system. For instance, in the example of FIG. 21, the expandable bulb 752 is sized to fit a camera 762, three channels 770a, 770b, 770c, and multiple optical fibers 771 for illumination. A specific example of the dimensions of the channels 770a, 770b, 770c is given in FIG. 21. More generally, the channels can have an inner diameter of between about 1 mm and about 3 mm, such as about 1 mm, about 1.5 mm, about 2 mm, about 2.5 mm, about 3 mm, or another diameter. The expandable bulb 752 can be formed of an optically clear, flexible, biocompatible material, such as a clear, low durometer thermoplastic polyurethane.

Optical Windows Used with Neuroendoscopes

Figure 22A:
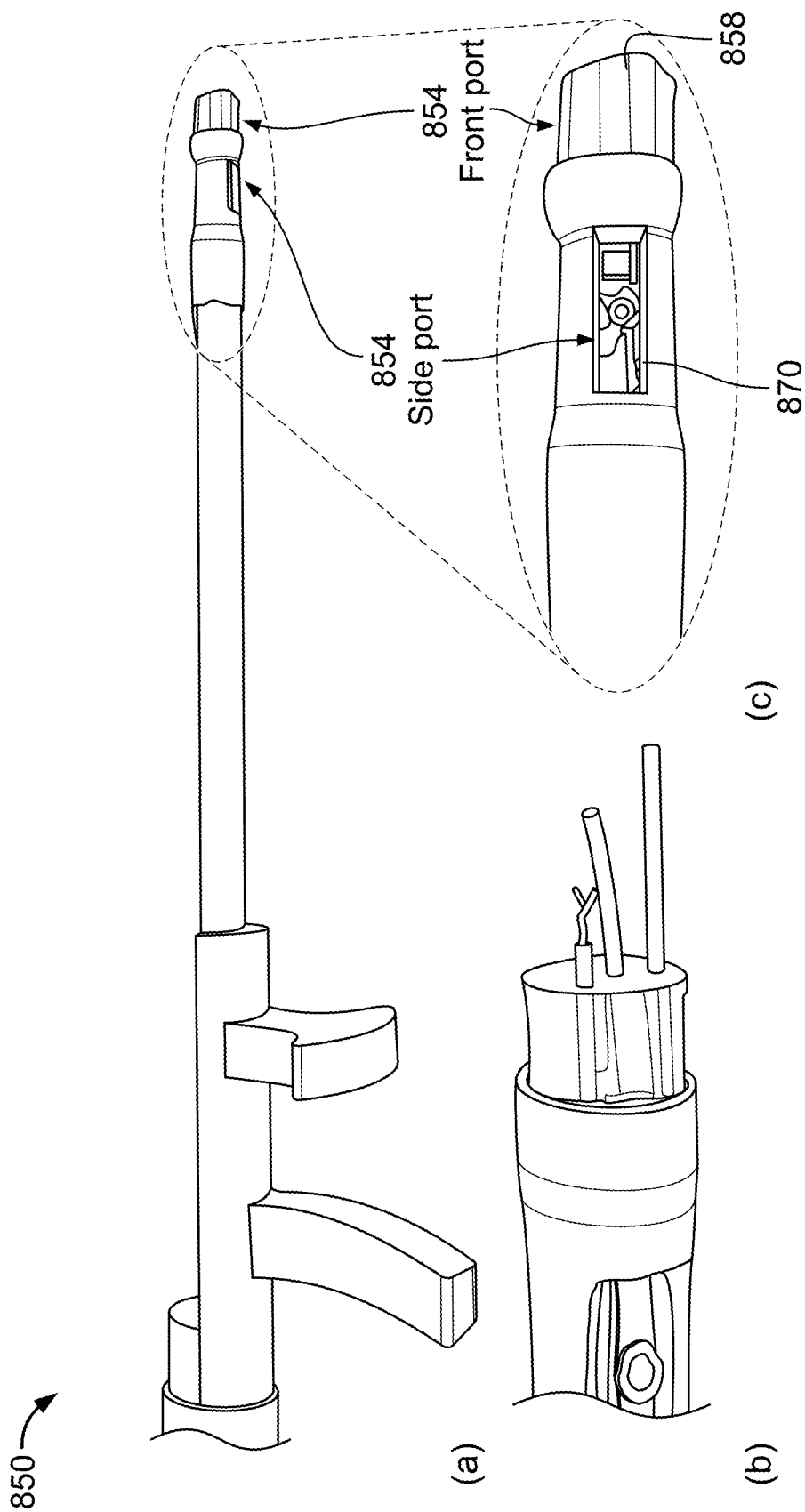
FIGS. 22A and 22B are photographs and a diagram, respectively, of a multi-port neuroendoscope having optical windows.
Figure 22B:
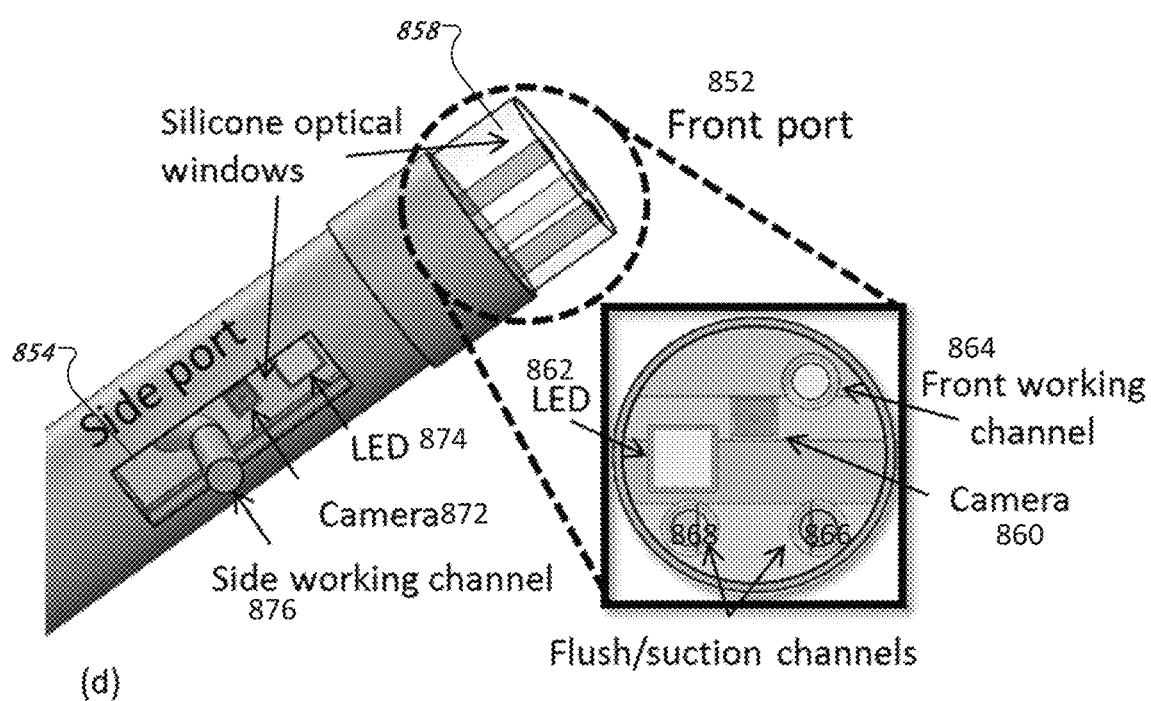

In some examples, the optical windows described here can be used in conjunction with a handheld neuroendoscope for image-guided neurosurgical procedures. Referring to FIGS. 22A and 22B, a handheld multi-port neuroendoscope 850 for image-guided neurosurgical procedures includes a distal imaging system 852 (sometimes also called a distal port) and a lateral imaging system 854 (sometimes also called a lateral port). The distal imaging system 852 includes an optically clear window 858 within which one or more cameras 860 and one or more light sources 862 are disposed. One or more channels are formed through the optical window 858. In the example of FIGS. 22A and 22B, a single tool channel 864 and two flushing channels 866, 868 are formed through the optical window 858. The lateral imaging system 854 also includes an optically clear window 870 within which one or more cameras 872 and one or more light sources 874 are disposed. One or more channels are formed through the optical window 870. In the example of FIGS. 22A and 22B, a single tool channel 876 is formed through the optical window 870.

The distal and lateral imaging systems 852, 854, respectively, enable the site of the neurosurgical procedure to be imaged, for instance, to assist in navigation of a tool to a desired site or visualization of the site before, during, or after the procedure. The ability to utilize one or both of a side channel (e.g., the side tool channel 876 or a side flushing channel) and a distal channel (e.g., the distal tool channel 864 or the distal flushing channels 866, 868) enables flexibility to access multiple surgical sites concurrently or to access the sample surgical site from different angles. In some examples, the neuroendoscope 850 can be used for procedures such as colloid cyst resection combined with septostomy. In some examples, the neuroendoscope 850 can be used for treating multiloculated hydrocephalus, where the side tool channel 876 enables the lysis of intraventricular adhesions that may be difficult to fenestrate through the distal tool channel 864.

The incorporation of multiple optical windows can enable multi-directional imaging and tool deployment. For instance, a lateral port can be useful so that a user can avoid pivoting the neuroendoscope to access a surgical site. In a specific procedure, a lateral port can be used to perform a septostomy with minimal pivoting of the instrument shaft. In another specific example, a lateral port can be used to enable multiplanar fenestration of the fibrous septae, which cannot generally be accessed easily by the tip port.

The optical windows 858, 870 have generally the characteristics described above with respect to the optical window 110. The optical windows 858, 870 can be formed of a solid, transparent material having a face that can conform to the topology of the tissue at the surgical site, thus displacing blood from the interface between the face of the optical window and the tissue at the surgical site and creating an optically clear path for imaging the tissue. In some examples, the optical windows 858, 870 can be formed of a transparent, compliant, biocompatible material, such as a polymer, glass, transparent crystals, or another transparent, compliant polymer. The optical windows 858, 870 can be formed of a material having a refractive index similar to the refractive index of cerebrospinal fluid, which is 1.33, in order to reduce distortion. For instance, the optical window can be formed of optically clear silicone (QSil 216 or QSil 218, Quantum Silicones).

In some examples, the distal optical window 858 and the lateral optical window 870 can have different thicknesses, e.g., in order to satisfy different design criteria for the two positions, in order to be functional for different uses, or for other reasons. For instance, the lateral optical window 870 can be designed to be flush with the outer surface of the neuroendoscope 850 so that no protrusions are present along the outer surface, e.g., the lateral optical window 870 can have a thickness of about 1 mm, about 2 mm, or another thickness, and can be molded to be flush with the surface. The distal optical window 858 can be thicker than the lateral optical window, e.g., about 3 mm thick, about 4 mm thick, about 5 mm thick, about 6 mm thick, or another thickness, in order to enable visualization of tools inserted into the tool channel 864 or to enable safe contact between the optical window 858 or tools and tissue at the surgical site.

In the example of FIGS. 22A and 22B, each optical window 858, 870 has a single tool channel formed therethrough. In some examples, multiple tool channels can be formed through each optical window, such as two tool channels, three tool channels, four tool channels, or another number of tool channels. Multiple tool channels can be useful, e.g., for complex surgical procedures involving the concurrent use of multiple tools, e.g., for colloid cyst dissection. The optical windows 858, 870 can include one or more flushing channels or can include no flushing channels. The channels can all be equally sized or each channel can have a different size or configuration. In some examples, a single tool channel can branch into multiple branches, e.g., multiple branches formed through a single optical window or through different optical windows. Branched tool channels can save cross sectional area when multiple ports are used.

The use of a CMOS camera in each of the optical windows 858, 870 can make the neuroendoscope 850 lighter and less bulky than a neuroendoscope employing a CCD camera or a rod lens. For instance, the neuroendoscope of FIGS. 22A and 22B can have a weight of less than about 100 g, such as 40 g, 45 g, 50 g, 60 g, 70 g, 80 g, 90 g, 100 g, or another weight. Furthermore, a CMOS camera included in each of the optical windows 858, 870 causes the weight of the neuroendoscope 850 to be substantially evenly distributed along the length of the neuroendoscope, thus making the neuroendoscope easy to manipulate and stabilize during surgery.

In some examples, the multi-port neuroendoscope described here can have advantages. For instance, the optical windows enable a user to visualize where the tool is before the tool exits the neuroendoscope and as the tool exits the neuroendoscope, thus enhancing safety. The optical windows can also enable a user to visualize a surgical site even during bleeding. Blood is opaque, but, as described above, the optical windows allow an optically clear path to be created between the optical window and the surgical site. In neurosurgery, light pressure and/or cauterization can be used to stop venous bleeding. With the optical windows, a user can visually explore for the source of bleeding, and can optically see the site in order to apply pressure and/or cauterize bleeding site.

In a specific example, intraventricular hemorrhage can be a fatal complication from endoscopic neurosurgical procedures. Bleeding inside the ventricle during surgery is often managed by local warm saline irrigation, by promoting vasospasm and thus hemostasis. The distal optical window of the multi-port neuroendoscope described here can exert even soft contact at the bleeding site, akin to application of gelfoam and cottonoid over bleeding veins and dural venous sinuses. Since the majority of intraventricular hemostasis during neurosurgical operations is performed without tissue contact, warm saline irrigation is the primary method of controlling minor hemorrhages, while bipolar coagulation is used for larger bleeding sites. The multi-port neuroendoscope gives an opportunity to offer focal soft contact pressure at the bleeding sites, especially venous hemorrhage.

In some examples, the neuroendoscope can be MR (magnetic resonance) compatible, enabling the neuroendoscope to be used in procedures involving endoscopic and MR guidance. "In the treatment of multi-loculated hydrocephalus, for example, MR imaging can reveal the extent and direction of intraventricular septations and periventricular cavitations with respect to the nearest cisterns, so as to enable fenestration of these optically occluded tissues resulting in a functioning cysto-ventriculo-cisternostomy. Another potential application leveraging multiple endoscopic ports and MR compatibility is transventricular biopsy, resection or laser ablation of periventricular lesions. This approach could be particularly beneficial in treating multiple lesions since standard ventricular access is straightforward and relatively safe compared with a more time-consuming preoperative planning and traversal of multiple paths through the brain parenchyma. In addition, endoscopic imaging could enhance effectiveness by providing optical imaging of tumor margins and also safety by enabling real-time visualization of intraprocedural hemorrhage and tool-based hemostasis."

EXAMPLES

The invention is further described in the following examples, which do not limit the scope of the invention described in the claims.

The following examples demonstrate the ex vivo and in vivo use of an instrument including an optical window and a tissue removal tool for precise removal of endocardial and myocardial tissue from the interior of a beating porcine heart. Other examples demonstrate the use of a neuroendoscope including multiple optical windows.

Example 1—Cardioscope Deployment in Ex Vivo Pulsatile Heart

Ex vivo removal of endocardial and myocardial tissue from the interior of the heart was performed using porcine hearts acquired at a local slaughterhouse. Porcine hearts were submerged in a water tank and connected to a pulsatile pumping system allowing both constant pressurization of the left ventricle and a simulated pumping motion, thus mimicking in vivo conditions in an ex vivo beating heart environment. Referring to FIG. 9, the instrument 400 including a tissue removal tool was inserted into the heart through the free wall 402 of the right ventricle 404 to remove excess tissue in the infundibulum 406 below the pulmonary valve 408.

Referring to FIGS. 23A and 23B, to enable evaluation of the precision of the tissue removal, a waterproof blue pen was used to demark a 15 mm diameter circle 806 on the infundibulum 802 of the heart. An instrument 800 including a tissue removal tool was then inserted through an incision in the right ventricular free wall 804 of the heart. As shown in FIG. 23B, a purse string suture 808 was used to seal the opening of the incision around the instrument 800.

Both endocardial and myocardial tissue were removed. Endocardial tissue is the thin, elastic layer lining the inside of the heart. Endocardial tissue tends to tear off in patches that can jam a tissue removal tool. Myocardial tissue lies below endocardial tissue and is more easily cut into small pieces. Based on the results of tissue removal from multiple hearts using the cardioscope, it was determined that layer-by-layer tissue removal was the fastest tissue removal technique that also avoided jamming of the tissue removal tool in the cardioscope.

To remove endocardial tissue, the cutting depth of the tissue removal tool was set to 0.3 mm and the tool rotational speed was set to 1000 rpm. These settings resulted in the generation of small pieces of endocardium, thus avoiding jamming of the tissue removal tool. After the endocardial tissue was removed from the region of interest, the cutting depth was increased to 0.8 mm and the tool rotational speed was decreased to 600 rpm. These settings resulted in a rapid rate of myocardial tissue removal.

FIGS. 23C and 23D show regions 810, 812 of endocardial and myocardial tissue removal, respectively. The imaging capabilities provided by the cardioscope enabled the surgeon to limit tissue removal to within the region marked by the circle 808. The time to remove the tissue as shown in FIGS. 23C and 23D was 6 minutes, 25 seconds.

Example 2—In Vivo Cardioscope Deployment

Figure 24:
FIG. 24 is a photograph of an in vivo beating heart experiment.

An in vivo experiment was performed on a 65 kg swine. To mimic the tissue removal performed for subvalvular stenosis, tissue was removed in two regions of the infundibulum to enlarge the outflow tract of the pulmonary valve. Referring to FIG. 24, the swine was placed on cardiopulmonary bypass and a small incision was made in the right ventricle free wall 902 of the swine heart. An instrument 900 including a tissue removal tool was inserted through the incision and the incision was sealed with a purse string suture.

Figures 25A, 25B, 25C, 25D, 25E, 25F:
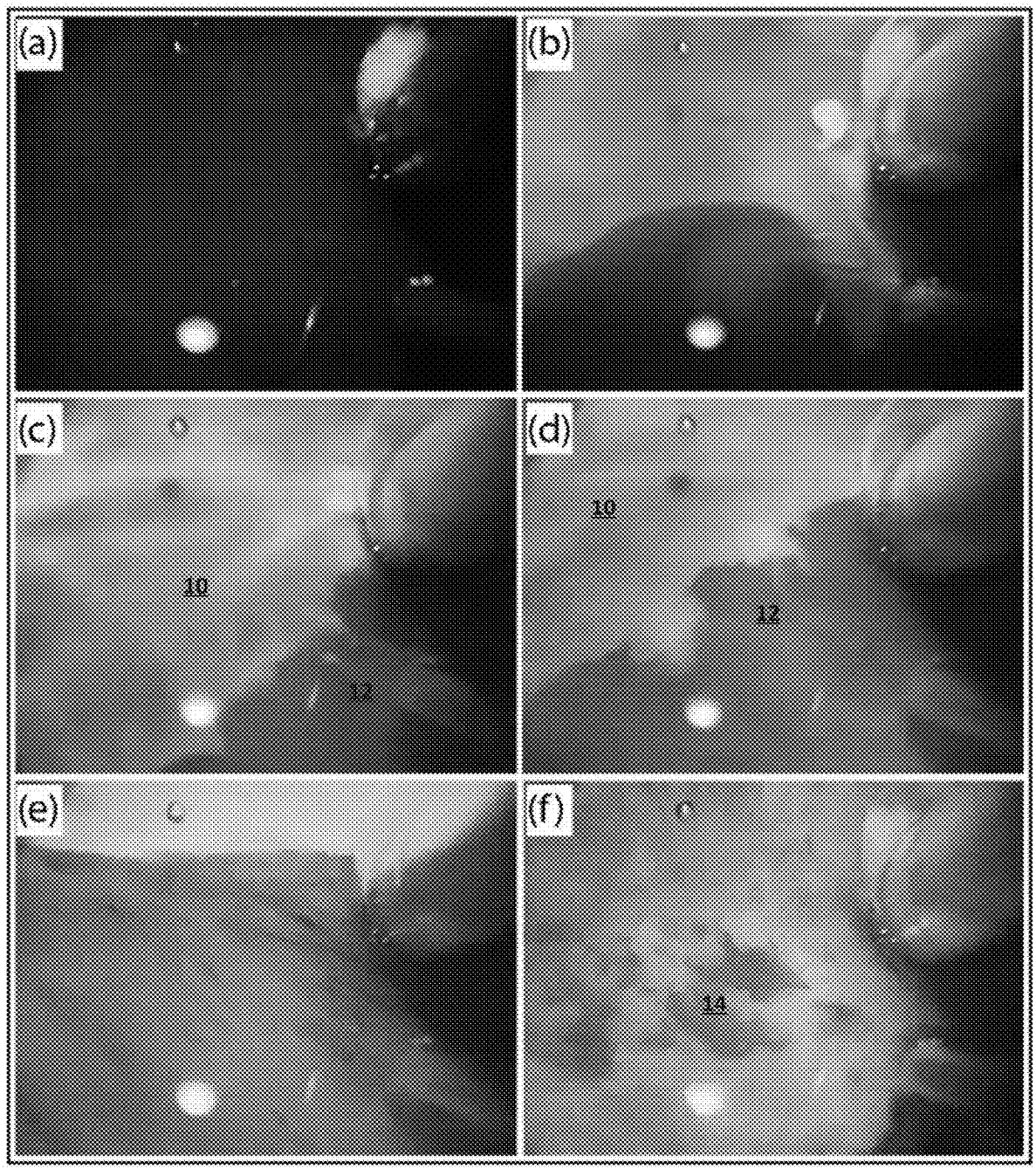
FIGS. 25A-25F are photographs of tissue removal in an in vivo beating heart experiment.

FIGS. 25A-25F show in vivo images of the beating heart acquired by the optical window of the instrument. FIG. 25A depicts the view in the blood-filled heart prior to contacting the heart tissue with the optical window of the instrument. As shown in FIG. 25B, when the optical window of the instrument is near, but not yet in contact with, the wall of the heart, saline dispensed from the flushing channel flushes blood away from in front of the optical window, temporarily providing a clear view of the adjacent heart tissue.

To remove endocardial tissue, the cutting depth of the tissue removal tool was set to 0.3 mm and the tool rotational speed was set to 1000 rpm. FIGS. 25C and 25D are images obtained by the optical window of the instrument during endocardium removal. The wide field of view provided by the optical window assists in determining the region of contact and provides detailed visual feedback on cutting progress. In FIGS. 25C and 25D, imaging shows that endocardial tissue 10 remains in the upper left of the field of view of the optical window but has been removed from a lower right region 12.

After the endocardial tissue was removed from the region of interest, the cutting depth was increased to 0.8 mm and the tool rotational speed was decreased to 600 rpm for removal of myocardial tissue. FIGS. 25E and 25F are images obtained by the optical window during myocardium removal. The image of FIG. 25F reveals that regions 14 of the myocardium have a tendency to fragment during removal.

Figures 26A, 26B, 26C:
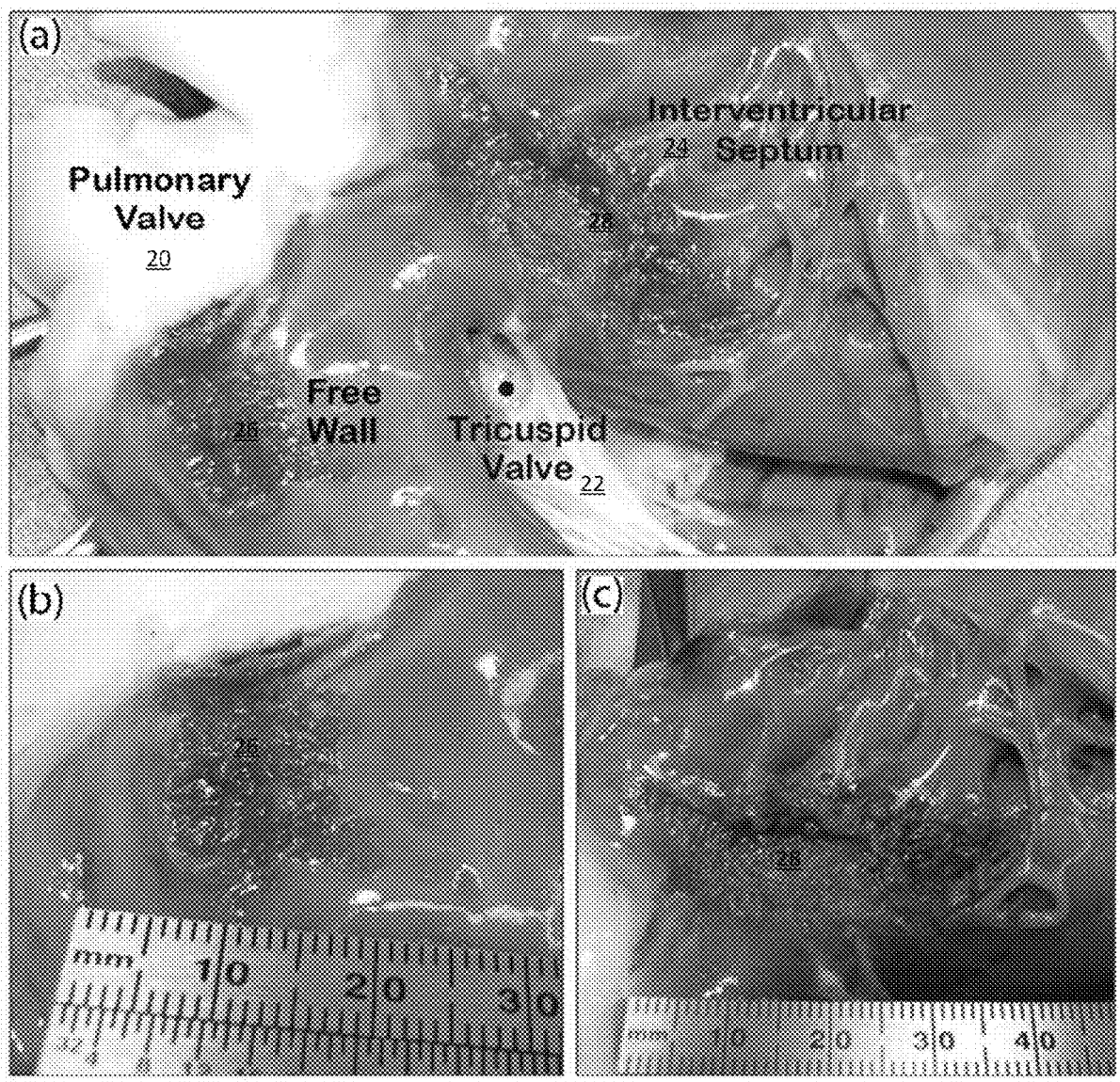
FIGS. 26A-26C are photographs of post-surgical evaluation of in vivo tissue removal from a beating heart.

The total tissue removal time was 3 minutes, 23 seconds and the procedure was well tolerated by the animal. Following the procedure, the animal was sacrificed and the heart was examined. Referring to FIGS. 26A-26C, the heart was cut open for visualization of the outflow tract of the pulmonary valve. FIG. 26A shows the pulmonary valve 20, the tricuspid valve 22, and the interventricular septum 24. Two regions 26, 28 in the outflow tract where tissue was removed can be seen. FIGS. 26B and 26C show close-up views of the regions 26, 28, respectively. The two regions 26, 28 of tissue removal measure 16 mm×10 mm and 20 mm×7 mm, respectively, and vary in depth up to 6 mm.

Irrigation and aspiration of the tissue removal tool were monitored during the tissue removal procedure. The total irrigation volume of heparinized saline was 210 mL and the volume of aspirated liquid was 130 mL. Hematocrit tests comparing a blood sample with the aspirated liquid indicated that only 8 mL of the aspirated liquid was blood, with the remainder being irrigation fluid. These results suggest that the optical window is effective in preventing the aspiration of blood by the tissue removal tool.

To evaluate entrapment of tissue debris, the aspirated liquid was filtered using a 40 micron cell strainer (BD Falcon™, Franklin Lakes, N.J.). The debris was examined under a microscope and weighed. The largest pieces of tissue debris were less than 3 mm long. The total debris weighed less than 39 mg, indicating that a significant amount of debris escaped into the bloodstream. The loss of debris into the bloodstream can be remedied by inserting an embolic filter in the pulmonary artery during the tissue removal procedure.

Figure 27:
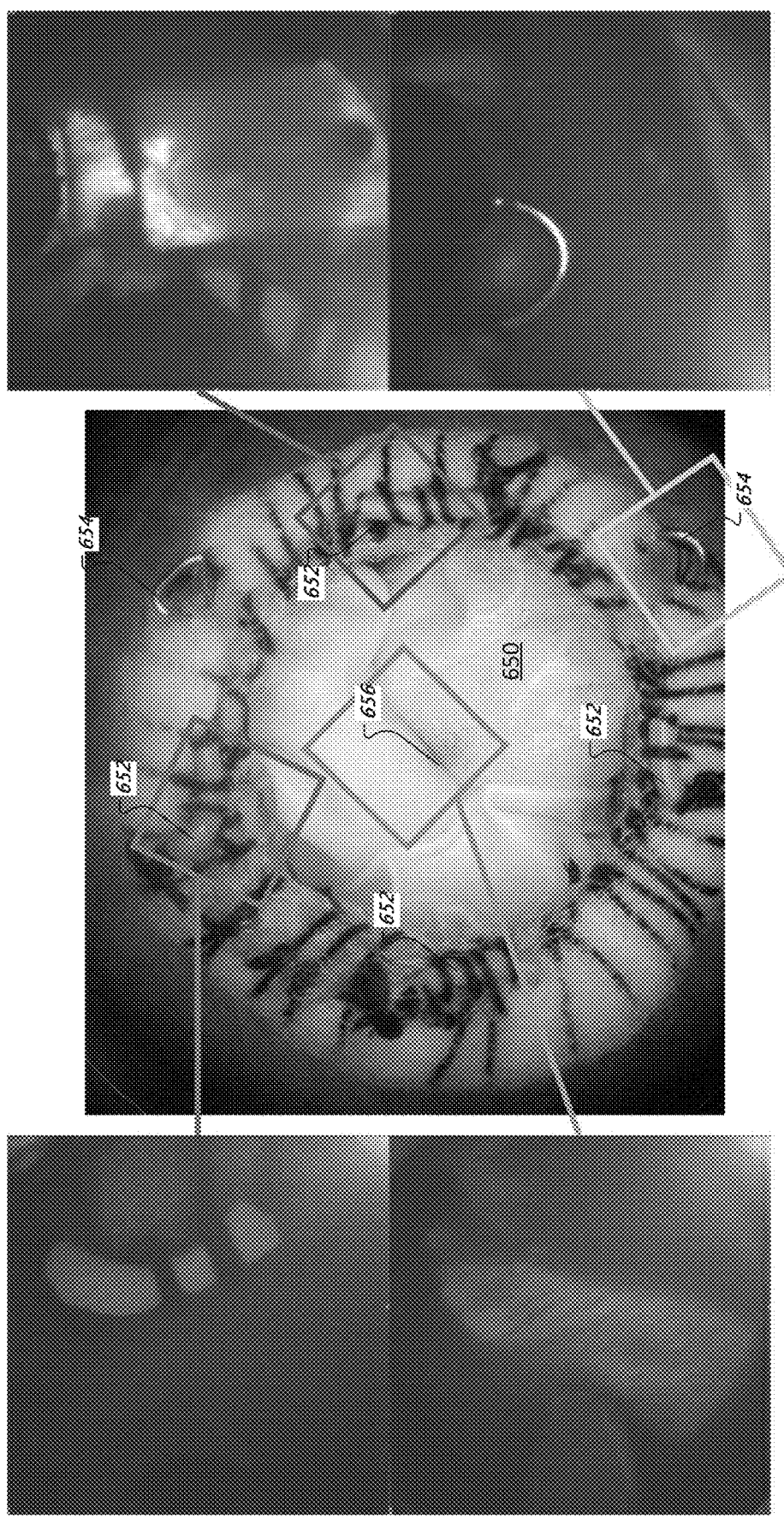
FIG. 27 shows images of a replacement aortic valve installed in a pig.

Referring to FIG. 27, in another in vivo example, a replacement aortic valve 650 was surgically installed in the heart of a pig. Four fiducial markers 652 were positioned on the bottom part of the valve for intraoperative guidance. Two metal rings 654 were integrated into the valve 650 to create paravalvular leakleakleaks when implanted.

While the pig heart was beating, a cardioscope mounted on the distal tip of a concentric tube robotic catheter was inserted into the left ventricle from the apex of the heart. Images of the valve 650 were taken from the ventricle using the cardioscope. In particular, the cardioscope was used to acquire images of two of the fiducial markers 652, one of the rings 654, and a bioprosthetic leaflet 656 made of pig pericardium.

Example 3—Multi-port Neuroendoscope Testing

The imaging capability of a multi-port neuroendoscope having a distal optical window and a lateral optical window designed for tissue resection at the distal end and electrocautery through the side port was tested and compared to the imaging capability of clinically used rigid and flexible neuroendoscopes. Referring to FIGS. 28A-28D, the neuroendoscope 450 included a straight 150 mm long plastic tube with a 7 mm outer diameter and an ergonomic handle on the proximal end thereof. The distal end of the neuroendoscope 450 included a distal optical window 456 having three, 1 mm diameter channels 458, 460, 462 positioned close to the corners of the field of view of a camera 464 housed in the optical window 456. Illumination was provided by a distal LED 466. These three channels 458, 460, 462 were used for tools, irrigation, and aspiration, respectively. A lateral optical window included a single 1 mm channel 468 with a 7 mm radius of curvature, sized to deliver a Bugbee wire to perform monopolar cautery for fenestration of the septum pellucidum. The lateral optical window 468 housed a side camera 470 and a side LED 472. All channels were lined by clear polyimide tubes having 1.2 mm outer diameter. Both the distal camera 464 and the side camera 470 were a 1 mm×1 mm×1 mm CMOS video camera (250×250 pixels, NanEye, Awaiba, Inc.), and both the distal LED and the side LED were a 1.6 mm×1.6 mm device (Cree Inc., Durham, N.C.).

Imaging of test targets was performed at multiple clinically-relevant standoff distances (contact, 5 mm, 10 mm, 15 mm, and 20 mm) through both the distal optical window and the lateral optical window. Imaging was also performed using clinically used straight rod-lens and flexible neuroendoscopes. The "USAF 3-bar Resolving Power Test target" (1951) was used as a standard reference in imaging testing. The target was printed on white paper using a 1200 dpi printer.

Figure 29:
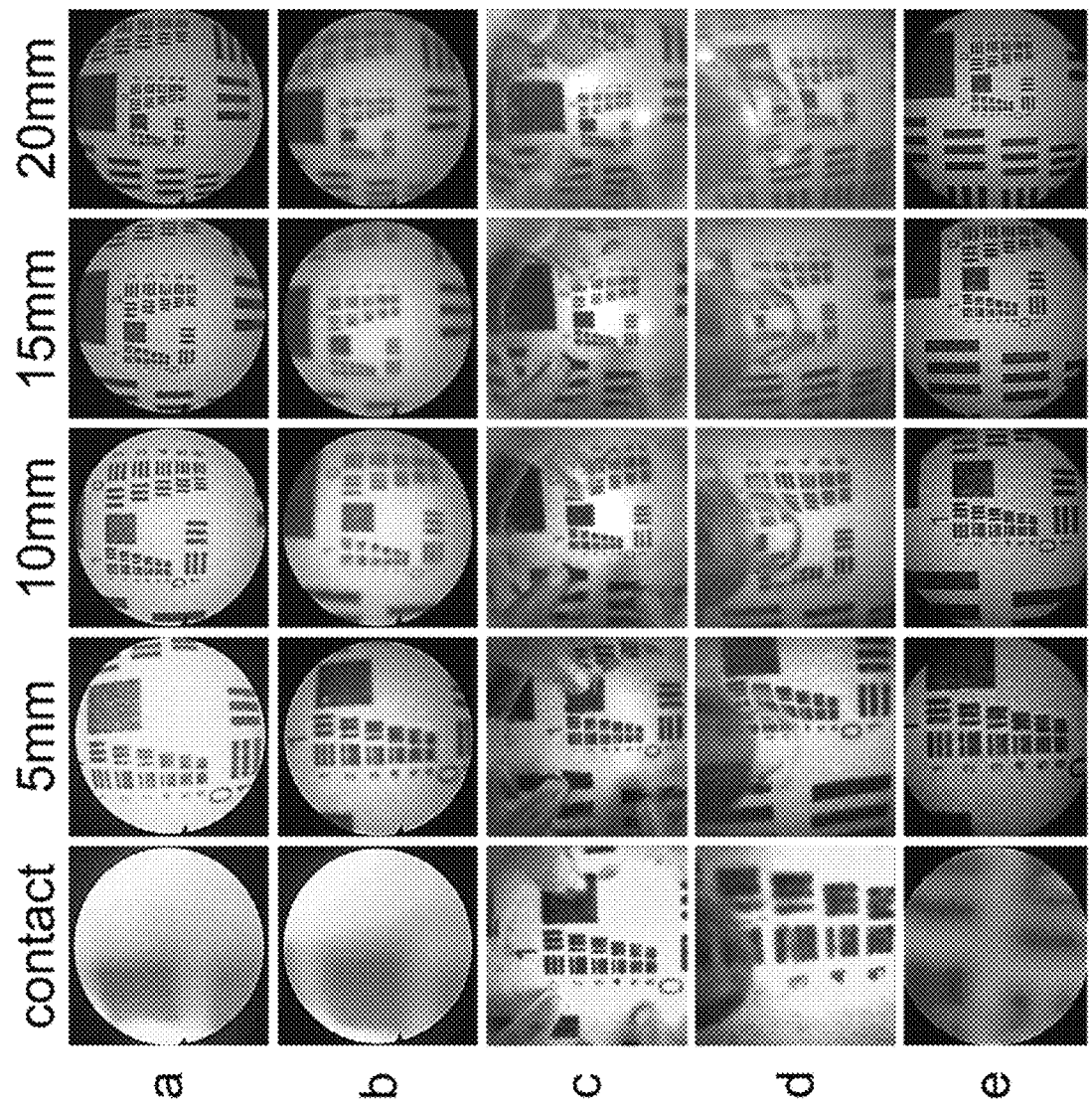
FIG. 29 shows images of an imaging target taken using various types of neuroendoscopes.

Referring to FIG. 29, images were obtained using the multi-port neuroendoscope having distal and lateral optical windows (sometimes referred to as the multi-port neuroendoscope) and clinically used rigid and flexible neuroendoscopes at various stand-off distances between the neuroendoscope and the imaging target. Since fiber-based neuroendoscopes are often used slightly defocused to avoid visualization of the boundaries of individual fibers, FIG. 30 provides both types of images for comparison. Rows (a) and (b) include crisp and blurred images obtained by a flexible neuroendoscope, respectively. Rows (c) and (d) include images obtained through the distal optical window and the lateral optical window, respectively, of the multi-port neuroendoscope. Row (3) includes images obtained by a rigid lens straight clinical endoscope. In contact with the imaging target, only the multi-port neuroendoscope provided a clear, focused view of the imaging target. For all non-contact distances, the image quality of the multiport endoscope was between that of the rigid scope and the flexible scope.

The MRI (magnetic resonance imaging) compatibility of multi-port neuroendoscope was evaluated by testing the neuroendoscope inside a scanner. MR compatibility testing included three components: testing for dangerous magnetic forces or torques as the neuroendoscope was introduced into and manipulated inside the bore of the MR scanner; determining the size of any MR artifacts produced by the neuroendoscope in surrounding tissue; and ensuring normal operation of the cameras in the neuroendoscope inside the MR scanner. These tests demonstrated the capability to both obtain MR images of tissue adjacent to the multi-port neuroendoscope and to stream video images from the neuroendoscope from within the MR scanner.

For MR compatibility testing, a multi-port neuroendoscope was inserted manually into the bore of an MR scanner (Skyra 3T, Siemens) and moved throughout the interior of the bore. Cephalic MRI was performed in a freshly sacrificed adult female Yorkshire pig (*Sus scrofa domesticus*). After evaluating the brain anatomy, the endoscope was advanced trans-cranially through a pre-positioned burr hole into a lateral ventricle inside the scanner bore. MR images were acquired using standard neurosurgical imaging sequences including of T2 weighted FLAIR. Separately, endoscope video sequences were acquired with and without simultaneous MR pulse sequence execution using the test targets to more easily detect any changes in image quality during scanning.

When the multi-port neuroendoscope was inserted into the bore of the MR scanner and moved manually, no magnetic forces were perceived, and video stream from the neuroendoscope was unaffected by placement inside the bore. When pulse sequences were executed during video streaming, the radio frequency (RF) portion of the pulse sometimes interfered with video streaming. It is believed that this interference may have been because the cameras of the neuroendoscope were not RF shielded. Images of the neuroendoscope inside a porcine brain were recorded and are shown in FIG. 30. The neuroendoscope appears as a void in these images. While artifacts of instruments in MR images are often larger than the instruments themselves, the size of the neuroendoscope artifact corresponds to the actual size of the neuroendoscope.

To evaluate the capability of the multi-port neuroendoscope in the context of a multi-port procedure, a combined colloid cyst resection and septostomy were performed in a cadaver head. After creating a frontal burr hole on a human cadaver skull and a cruciate durotomy, an obturator was introduced into the parenchyma to evaluate imaging in the presence of blood. The cavity was filled with blood and a multi-port neuroendoscope was introduced. To determine if the distal and lateral optical windows of the neuroendoscope would enable visualization of tissue during contact with tissue, the neuroendoscope was slowly advanced until contact was made between the distal optical window and the tissue.

Considering the fixed shrunken cadaveric ventricular anatomy, a 4-burr-hole craniotomy was made to implant an artificial colloid cyst trans-callosally at the left foramen of Monro. To make the colloid cyst phantom, 0.05% ultra-pure agarose (Life Technologies, CA) was dissolved in 1×PBS by boiling in micro oven and cooled down to 45° C., before adding cheese cream for whitish color. Immediately, the whole mixture was poured into a stretched Parafilm (Neenah, Wis., USA), to simulate a colloid cyst with whitish viscous contents that can be readily aspirated. Septostomy was performed inside the cadaver head using a Bugbee wire inserted through a tool channel of the lateral optical window of the multi-port neuroendoscope under direct vision. The scattered cadaver debris in the ventricles obscured the views for both a standard endoscope and the multi-port neuroendoscope. Consequently, a phantom test bed was made in a clear saline-filled container to perform cutting, suction and irrigation on the colloid cyst phantom.

The ability of the multi-port neuroendoscope to visualize tissue while in contact with tissue is illustrated in FIGS. 31A and 31B. As with a standard scope, nothing can be seen in a blood-filled cavity (FIG. 31A). Once soft contact is made with the tissue, however, the silicone optical window displaces the blood in front of the camera, making clear visualization possible (FIG. 31B).

Figures 32A, 32B, 32C, 32D, 32E, 32F:
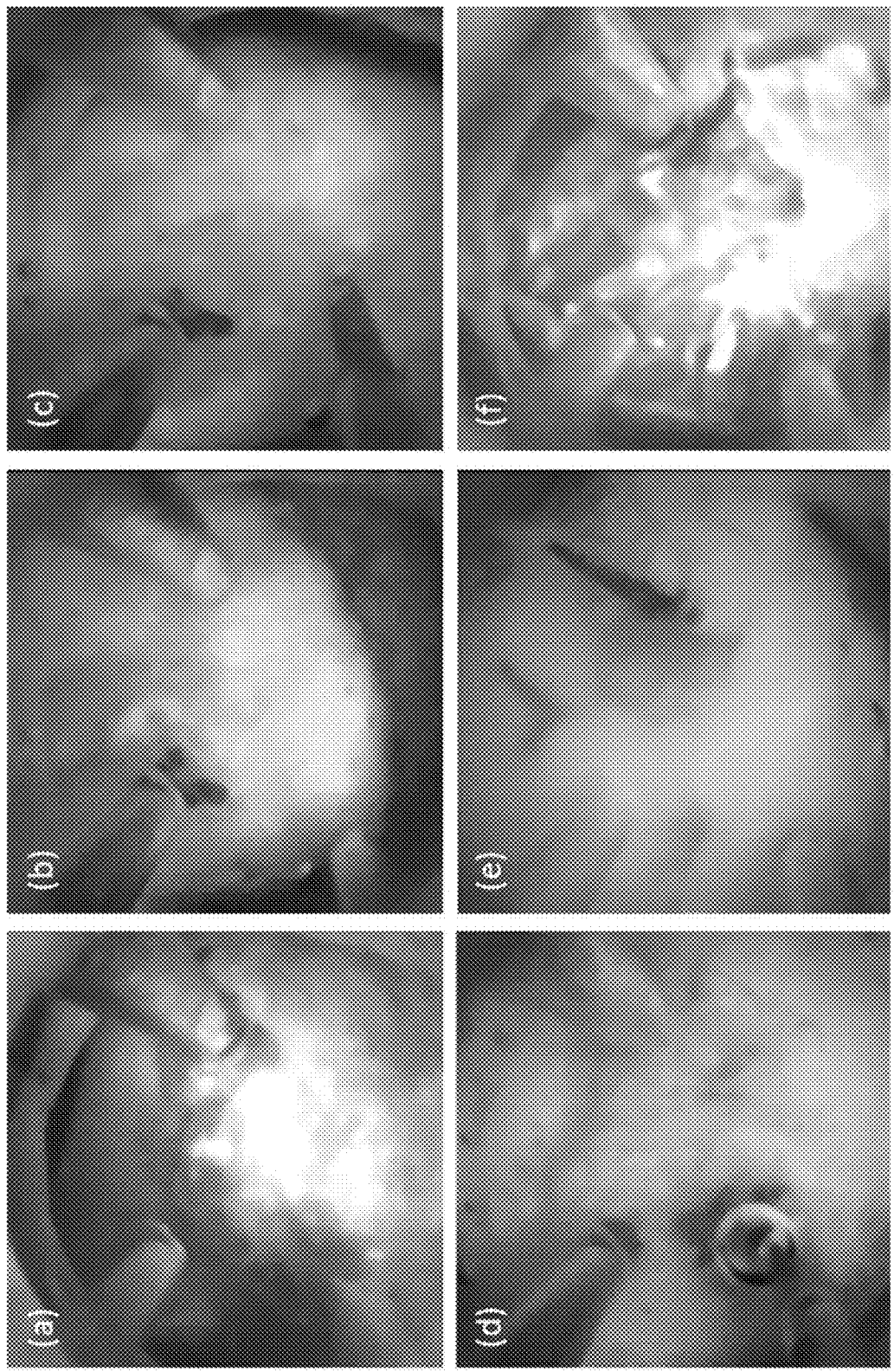
FIGS. 32A-32F are photographs acquired during fenestration and aspiration of a colloid cyst using a multi-port neuroendoscope.

Fenestration and aspiration of a colloid cyst using a multi-port neuroendoscope was demonstrated in a phantom test bed. Endoscopic tip views of the classic skill sets of cutting, suction and irrigation on the colloid cyst phantom are shown in FIGS. 32A-32F, captured by the camera housed in the distal optical window of the multip-port neuroendoscope. In particular, FIG. 32A is an image of two channels formed in the distal silicone optical window. FIGS. 32B and 32C are images of endoscopic graspers used to hold the capsule. FIGS. 32D and 32E are images of suction and irrigation, and FIG. 32F is an image following emptying of the cyst contents off the capsule.

Figures 33A, 33B, 33C, 33D, 33E:
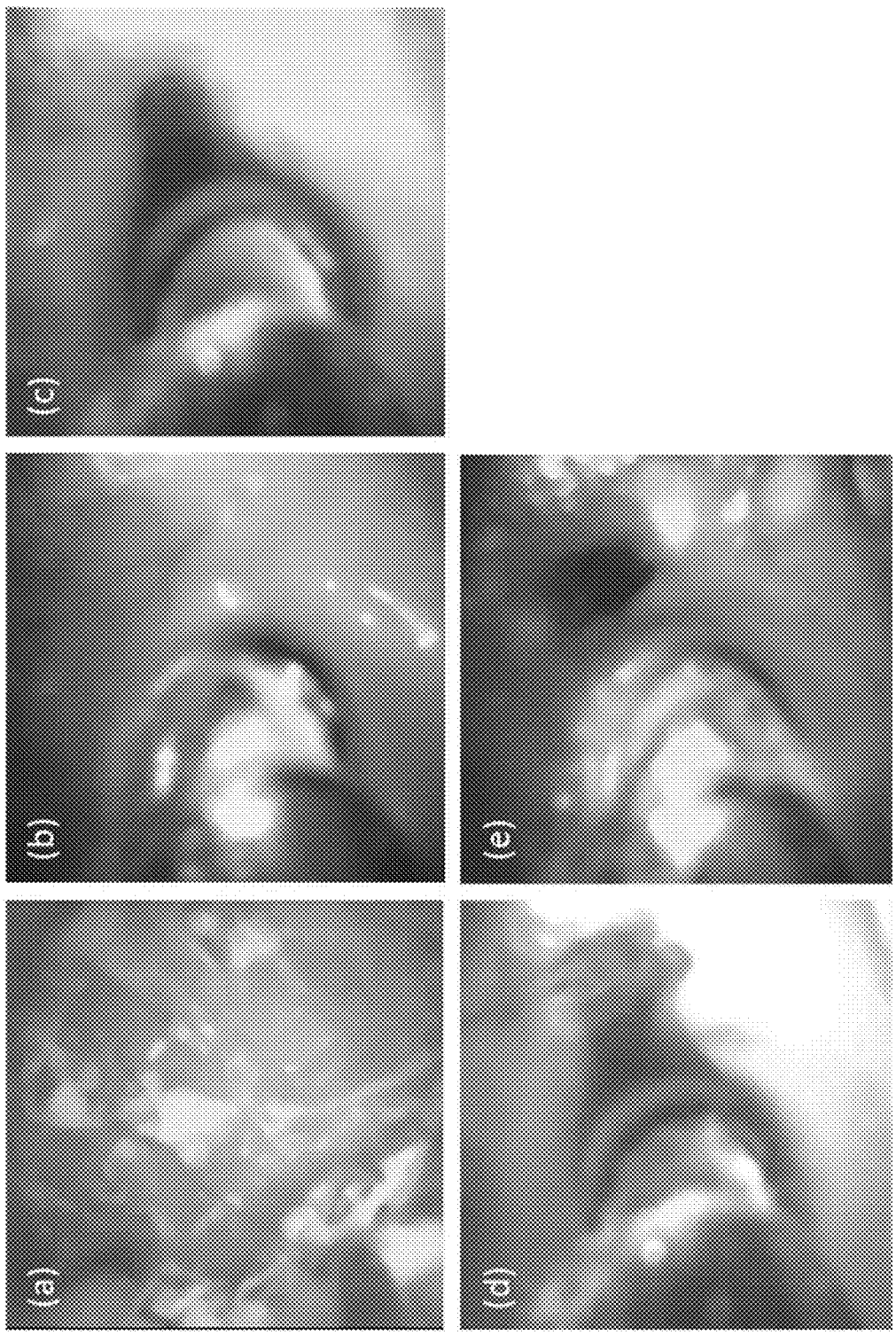
FIGS. 33A-33E are photographs acquired during septostomy using the lateral port of a multi-port neuroendoscope.

Referring to FIGS. 33A-33E, the lateral port of the multi-port neuroendoscope was used to perform septostomy inside the cadaver head while maintaining a stable view of the anterior field near the colloid cyst phantom at the foramen of Monro. FIG. 33A shows a close-up view through the distal optical window of the membranous capsule of the colloid cyst phantom. FIGS. 33B-33E are images of the sequential septostomy steps of advancing the lateral port of the neuroendoscope toward the septum, passing the Bugbee wire through a channel of the lateral optical window (FIG. 33C), and firing the coagulation probe to coagulate the septum (FIG. 33D). FIG. 33E is an image of the septostomy hole.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for performing a surgical or interventional procedure, the device comprising:
multiple extending members configured to together grip tissue during the surgical or interventional procedure, at least a first extending member of the multiple extending members comprising, integrated into a tissue-grasping surface of the first extending member, a solid optical window formed of a transparent, compliant material,
wherein the solid optical window comprises a proximal side and a distal side, wherein a distal face of the solid optical window is configured to contact the tissue during the surgical or interventional procedure; and an imaging system within the first extending member, the imaging system configured and positioned to obtain an image of a surface of the tissue pressed against the distal face of the solid optical window during the surgical or interventional procedure, wherein the image is obtained from within the first extending member through at least a portion of the distal face of the solid optical window, and wherein the imaging system comprises an imaging sensor embedded in the solid optical window, wherein the imaging sensor is spaced apart from the distal face of the solid optical window, and wherein the imaging sensor is configured to provide images of the surface of the tissue pressed against the distal face of the solid optical window during the surgical or interventional procedure, the images having sub-millimeter resolution.

2. The device of claim 1, wherein the distal face of the solid optical window is marked with one or more markings indicating lengths of tissue within a field of view of the imaging system.

3. The device of claim 1, wherein a compliance of the transparent, compliant material is such that the material conforms with irregular surfaces of the tissue.

4. The device of claim 1, wherein a tool channel is defined through the solid optical window from the proximal side to the distal side of the solid optical window, wherein the tool channel is configured to receive a tool for performing the surgical or interventional procedure.

5. The device of claim 4, wherein the tool channel has a visibility that allows the tool to be imaged by the imaging system as the tool is deployed through the tool channel.

6. The device of claim 4, comprising a tube disposed in the tool channel.

7. The device of claim 4, wherein the transparent, compliant material is configured to form a seal positioned at a distal opening of the tool channel when the tool is inserted through the distal opening.

8. The device of claim 4, wherein the tool channel is configured to be filled with saline prior to insertion of the tool into the tool channel.

9. The device of claim 1, wherein the solid optical window is formed from silicone or silicone rubber.

10. The device of claim 1, wherein the solid optical window is formed from a polymer.

11. The device of claim 1, wherein the imaging system comprises one or more cameras or optical fibers.

12. The device of claim 1, wherein the imaging system is disposed adjacent to the solid optical window.

13. The device of claim 1, wherein the multiple extending members form forceps.

14. The device of claim 1, wherein the multiple extending members form a cardiac valve leaflet grasper.

* * * * *